(12) United States Patent
Schwartz et al.

(10) Patent No.: US 10,857,357 B2
(45) Date of Patent: Dec. 8, 2020

(54) SYSTEM FOR IMPLANTING, ACTIVATING, AND OPERATING AN IMPLANTABLE BATTERY

(71) Applicant: BONE LIFE LTD., Caesarea—North Industrial Park (IL)

(72) Inventors: Liat Schwartz, Haifa (IL); Valentin Barsky, Haifa (IL)

(73) Assignee: BONE LIFE LTD., Caesarea—North Industrial Park (IL)

( * ) Notice: Subject to any disclaimer, the term of this patent is extended or adjusted under 35 U.S.C. 154(b) by 94 days.

(21) Appl. No.: 16/038,685

(22) Filed: Jul. 18, 2018

(65) Prior Publication Data

US 2019/0009082 A1   Jan. 10, 2019

Related U.S. Application Data

(63) Continuation of application No. 15/404,894, filed on Jan. 12, 2017, now abandoned, which is a continuation of application No. 12/714,563, filed on Mar. 1, 2010, now abandoned, which is a continuation-in-part of application No.
(Continued)

(30) Foreign Application Priority Data

Aug. 30, 2007  (IL) .......................... 185637
Mar. 2, 2009   (IL) .......................... 197357

(51) Int. Cl.
*A61N 1/30* (2006.01)
*A61N 1/378* (2006.01)
*A61N 1/05* (2006.01)

(52) U.S. Cl.
CPC ............... *A61N 1/306* (2013.01); *A61N 1/05* (2013.01); *A61N 1/378* (2013.01)

(58) Field of Classification Search
CPC .. A61N 1/0428; A61N 1/0432; A61N 1/0436; A61N 1/30; A61N 1/306; A61N 1/325
See application file for complete search history.

(56) References Cited

U.S. PATENT DOCUMENTS

| 2,069,112 A | 1/1937 | Oppenheim |
|---|---|---|
| 3,784,908 A | 1/1974 | Anderson |

(Continued)

FOREIGN PATENT DOCUMENTS

| WO | 2009027968 | 3/2009 |
|---|---|---|
| WO | 2010100637 | 9/2010 |

OTHER PUBLICATIONS

Communication pursuant to Article 94(3) EPC dated May 28, 2013, from the European patent office re: Application No. 10748409.9.
(Continued)

*Primary Examiner* — Tammie K Marlen
(74) *Attorney, Agent, or Firm* — Roach, Brown, McCarthy & Gruber, P.C.; Kevin D. McCarthy

(57) ABSTRACT

Apparatus, systems, and methods for the treatment of bone, cartilage and other types of hard tissue. The treatments, which are suitable for extended treatment, include the treatment and prevention of pathologies through the controllable use of silver, iron, zinc, or magnesium ions. These pathologies may include a pathology which is at least partially induced or aggravated by an infectious disease, for example a bacterial disease. In this case the electrically released ions are silver ions, which are known to have antibacterial properties.

18 Claims, 20 Drawing Sheets

Related U.S. Application Data

PCT/IL2010/000150, filed on Feb. 22, 2010, and a continuation-in-part of application No. PCT/IL2008/001157, filed on Aug. 28, 2008.

(56) References Cited

U.S. PATENT DOCUMENTS

| | | | |
|---|---|---|---|
| 4,027,393 | A | 6/1977 | Ellis |
| 4,126,937 | A | 11/1978 | Ellis |
| 4,313,438 | A | 2/1982 | Greatbatch |
| 4,314,554 | A | 2/1982 | Greatbatch |
| 4,569,673 | A | 2/1986 | Tesi |
| 4,615,705 | A | 10/1986 | Scales |
| 4,886,075 | A | 12/1989 | Jones |
| 5,322,520 | A | 6/1994 | Milder |
| 5,395,398 | A | 3/1995 | Rogozinski |
| 5,814,094 | A | 9/1998 | Becker |
| 6,149,620 | A | 11/2000 | Baker |
| 6,663,634 | B2 | 12/2003 | Ahrens |
| 6,775,570 | B2 | 8/2004 | Joshi |
| 6,923,990 | B2 | 8/2005 | Capelli |
| 8,221,396 | B2 | 7/2012 | Dehnad et al. |
| 2002/0182485 | A1 | 12/2002 | Anderson |
| 2003/0167024 | A1 | 9/2003 | Imram |
| 2003/0204163 | A1 | 10/2003 | Marchitto |
| 2008/0147186 | A1 | 6/2008 | Joshi et al. |
| 2008/0195033 | A1 | 8/2008 | Eagleson |
| 2009/0054951 | A1 | 2/2009 | Leuthardt |

OTHER PUBLICATIONS

Communication under rule 71(3) EPC dated Mar. 29, 2012 from the European patent office re: Application No. 08789829.2.
Communication under rule 70(2) and 70a(2) EPC dated May 23, 2013 from the European patent office re: Application No. 08789829.2.
Communication under rule 70(2) and 70a(2) EPC dated May 23, 2013 from the European patent office re: Application No. 10748409.9.
Office action dated Aug. 26, 2012 form the Israel patent office re: applicaiton No. 197357 and its translation into English.
International Preliminary Report on patentability dated Mar. 2, 2010 from the international bureau of WIPO re: application No. PCT/IL08/01157.
International search report dated Sep. 1, 2010 from the international searching authority re: application No. PCT/IL10/00150.
International search report dated Dec. 18, 2008 from the international searching authority re: application No. PCT/IL08/01157.
Invitation to pay additional fees dated Jun. 22, 2010 from the international searching authority re: application No. PCT/IL10/00150.
Written opinion dated Sep. 1, 2010 from the international searching authority re: application No. PCT/IL10/00150.
Written opinion dated Dec. 18, 2008 from the international searching authority re: application No. PCT/IL08/01157.
Response dated Nov. 20, 2011 to Communication pursuant to rules 70(2) and 70a(2) EPC of May 23, 2011 from the European patent office re: application No. 08789829.2.
Communication pursuant to rules 161(2) and 162 EPC dated Apr. 14, 2010 from the European patent office re: application No. 08789829.2.
Office action dated Oct. 18, 2010 from the Israeli patent office re: application No. 185637 and its translation into English.
Webster et al., "Silver Anode Treatment of Chronic Osteomyelitis" Clinical Orthopaedics and related research, 161; 105-114, Nov.-Dec. 1981, abstract.
Lassarini et al., "Osteomyelitis in long bones", The journal of bone & joint surgery, 86-A(10): 2305-2318, Oct. 2004.
McCarthy et al., "Musculoskeletal infections in children, basic treatment principles and recent advancements", The journal of bone & joint surgery, 86-A(4): 850-863, Apr. 2004.
Supplementary European search report and the European search opinion dated May 4, 2011 from the European patent office re: 08789829.2.
Supplementary European search report and the European search opinion dated Aug. 7, 2012 from the European patent office re: 10748409.9.
Office action dated Aug. 10, 2012 from the Russian federal institute of industrial property of the federal intellectual property service for patent and trademarks, re: application No. 2010109024 and its translation in English.
Becker et al. "Treatment of Orthopaedic infections with electrically generated silver ions. A preliminary report" The journal of bone & joint surgery, American vol. 60-A(7): 871-881, Oct. 1978.
Cleveland clinic, "Osteomyelitis" The cleveland clinic foundation, retrieved from the internet, 1995-2005.
Dueland et al. "Silver antibacterial bone cement, comparison with gentamicin in experimental osteomyelitis" Clinical orthopaedics and related research, 169-264-268, Sep. 1982.
Hunt et al. "The effect of differing ambient oxygen tensions on wound infection" Annals of Surgery, 181(1): 35-39, Jan. 1975.
Mendel et al. "Therapy with hyperbaric oxygen and cefazolin for experimental osteomyelitis due to *Staphylococcus aureus* in rats" Jounrnal of undersea and hyberbaric and medical society, 26(3); 169-174, Fall 1999.
Nand et al. "Dual use of silver for management of chronic bone infections and infected non-unions" Journal of the Indian medical association, 94(3): 91-95, Mar. 1996, Abstract.
RWJUH "Osteomyelitis" Rover Wood Johnson University hospital, New Brunswick, NY USA, retrieved from the Internet, 2011.
Stallmann et al. "Osteomyelitis prevention in rabbits using antimicrobial peptide h1.F1-11- or gentamicin-containing calcium phosphate cement", Journal of antimicrobial chemotherapy, JAC, 54(2): 472-476, 2004.
Voguely et al., "Effects of hydrosyapatite coating on To-6A1-4B implant-site infection in a rabbit tibial model"; Journal of Orthopaedic research, 18(3): 485-493, May 2000 Abstract.
Wright, "Hyperbaric oxygen therapy for wound healing" Worldwide wounds, May 2001.
Zuluaga et al., "Lack of microbiological concordance between bone and non-bone specimens in chronic osteomyelitis: An observationsl Study" BMC Infectious disease, 2(8): 1-7, May 16, 2002.
International preliminary report on patentability dated Sep. 15, 2011 from the international bureau of WIPO re: application No. PCT/IL2010/000150.

240

260

280

18

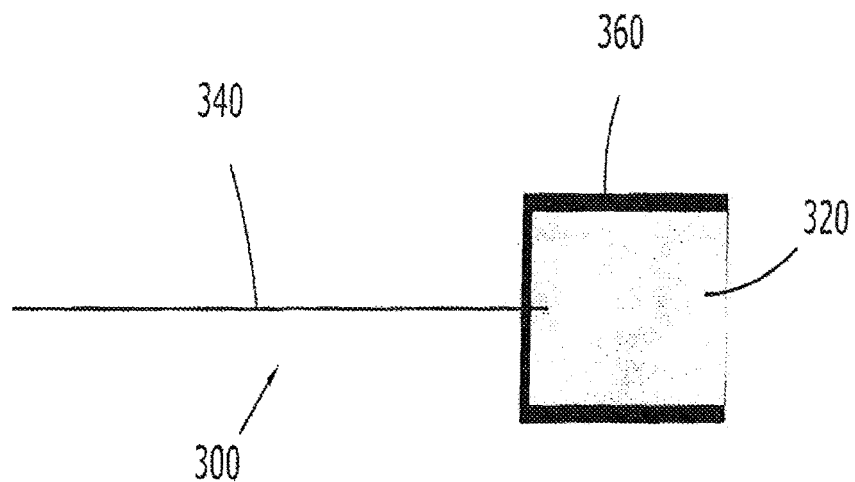
Fig. 10E
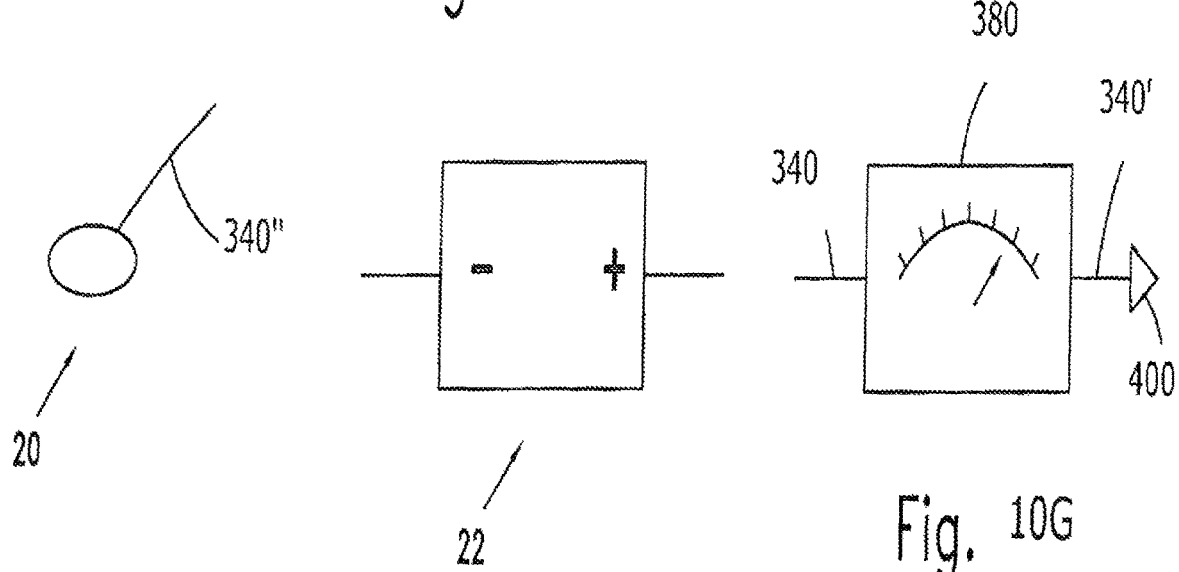
Fig. 10H
Fig. 10F
Fig. 10G

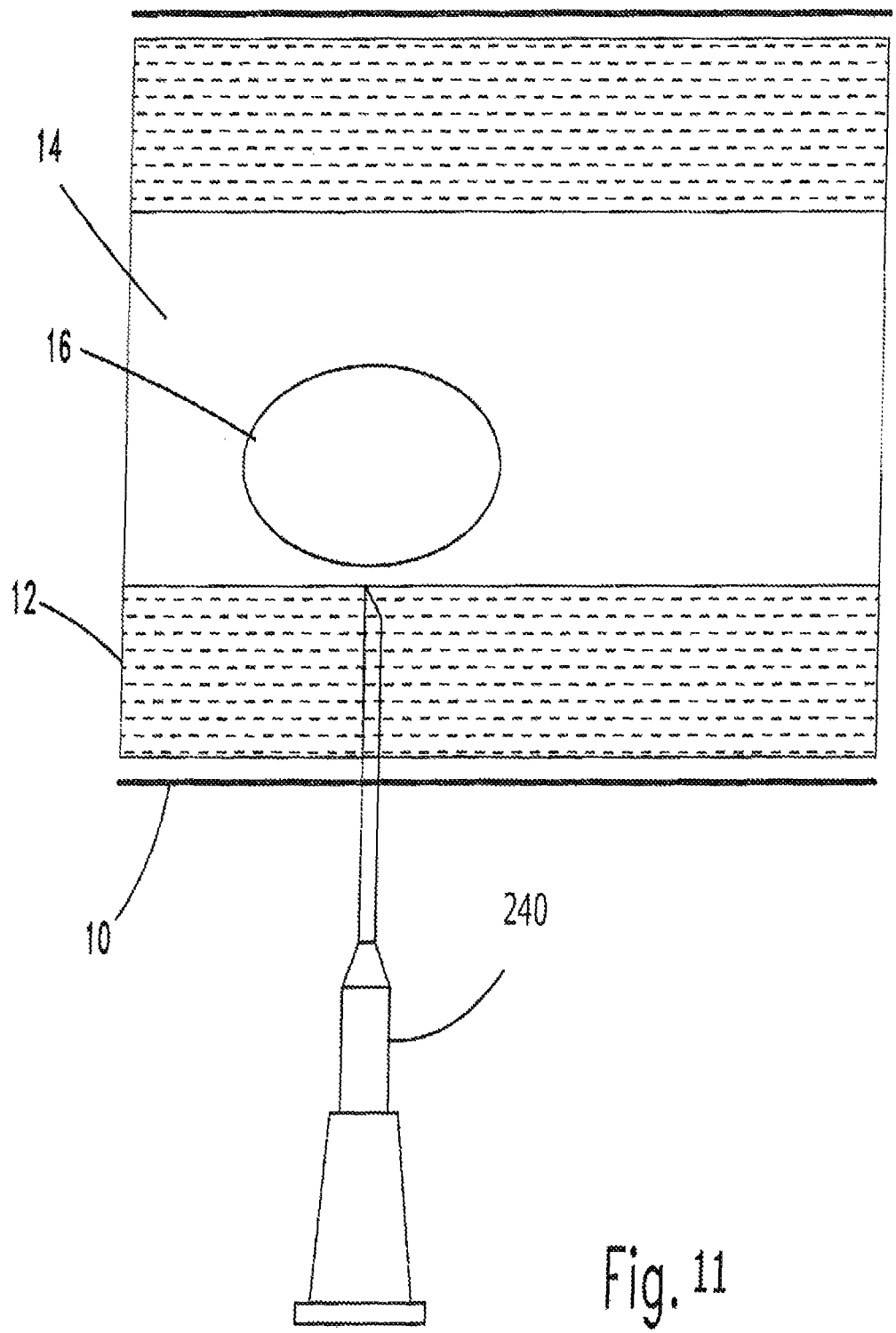

SYSTEM FOR IMPLANTING, ACTIVATING, AND OPERATING AN IMPLANTABLE BATTERY

CROSS-REFERENCE TO RELATED APPLICATIONS

This application is a continuation of U.S. patent application Ser. No. 12/714,563, filed Mar. 1, 2010, which is a continuation-in-part of: (a) PCT Patent Application No. PCT/IL2008/001157, filed Aug. 28, 2008, which claims priority to Israel Patent Application No. 185637, filed Aug. 30, 2007; and (b) PCT Patent Application No. PCT/IL2010/000150, filed Feb. 22, 2010, which claims priority to Israel Patent Application No. 197357, filed Mar. 2, 2009; all of which are hereby incorporated by reference as if fully set forth herein.

FIELD OF THE INVENTION

The invention is related to the field of medicine and medical devices. Specifically the invention relates to the field of treatment of bone, cartilage and hard tissue, including the treatment and prevention of pathologies thereof.

BACKGROUND OF THE INVENTION

In spite of very advanced diagnostic and treatment options, bone infection called Osteomyelitis remains one of the most serious complications in orthopedic surgery. On one hand it affects dramatically the quality of life of a patient and may risk his life. On the other hand it is a very expensive disease for the patient and society because of the involved costs of diagnosis, treatment, rehabilitation, lost of productivity and in many cases incomplete cure.

Osteomyelitis can affect all populations, infants, children, adults, and the elderly, while populations at increased risk include individuals with weakened immune system or other diseases increasing susceptibility to infections. It may be caused by a variety of microbial agents and situations, e.g. an open wound, soft tissue infection, an infection from elsewhere in the body, bacteria in the blood stream, etc.

If left untreated, the infection becomes chronic, and results in chronic Osteomyelitis (COM). COM is a major medical problem in most countries, mainly associated with violent trauma and orthopedic surgery. Its high impact is suffered equally in terms of increased morbidity, comprehensive use of health care resources and sequelae. In the opinion of authorized clinicians, the term cure cannot be applied to COM, because the bone infection may occur years after apparently successful treatment of the disease.

The objective of treating Osteomyelitis is to eliminate the infection and minimize any long-term complications. The main drawbacks of the currently used treatments, i.e. surgical debridement, locally applied antibiotics, or electrically liberated external silver ions, are their short term effect and restricted local influence. In many cases the infection spreads through the bone where the locally applied treatment does not reach. On the other hand, the prolonged systemic antibiotic treatment which is used in most cases is also not completely efficient, as it is not localized enough. Frequently, after the end of the treatment, infection reappears. Some cases of COM are so resistant to treatment that amputation may be required.

The use of silver and silver compounds in medicine has been recorded for thousands of years. Since the late 1800's the use of silver as a bactericide has been documented and studied intensively. Without going into too many details, representative examples of ways in which silver, and in particular silver ions, are administered to heal or prevent bacterial diseases are:

topical application; One well known example of the topical application of silver compounds is the use of silver sulfadiazine for the treatment of burns. As another example U.S. Pat. No. 6,923,990 describes stabilized compositions comprised of a silver-thiosulfate ion complex further complexed with an amine. In one embodiment, these compositions are incorporated into wound dressings.

coating or impregnating medical devices with silver containing materials; Embodiments of U.S. Pat. No. 6,923,990 are concerned with impregnating medical devices such as catheters with the silver-thiosulfate-amine compositions. U.S. Pat. No. 6,663,634 describes a bone screw on which at least part of the surface a thin coating of silver has been deposited. After the screw is installed in a bone, galvanic currents arise near the coated part of the screw, releasing silver ions in that region. Surgical implants comprising small amounts of biodegradable silver are described in U.S. Pat. No. 4,615,705.

thermocouple junctions; It is a known phenomenon that a localized electric current can be induced to flow when two pieces of dissimilar metals are brought into contact with each other. This phenomenon has been taken advantage of for many years in medicine, specifically in dental medicine. For example U.S. Pat. Nos. 2,069,112 ; 4,886,075 describe devices comprised of wires of two different metals, for example silver together with either gold or platinum that are twisted or soldered together and inserted into a root canal. As a result of the thermocouple effect, silver ions are released into the canal and surrounding tissue where they heal bacterial infections, help prevent their reoccurrence, and promote bone growth. The device can either be removed from the tooth after a period of time or sealed permanently in the tooth.

ion generators; Many publications describe methods of producing silver ions around surgical or dental devices in vivo in order to treat bacterial infections and/or to prevent their occurrence. In these devices an electrical circuit comprised of a constant current supply, a first electrode attached in some way to the device, and a second electrode either implanted in the soft tissue near by the first electrode or attached to the device and electrically insulated from the first electrode. The electrolytes in the body fluids complete the circuit when the current supply is activated. One of the electrodes is usually silver and the electric current flowing in the circuit releases silver ions into the body fluids. The silver ions are only released as long as the current source is activated. The principle of the operation of such devices can be understood from, for example U.S. Pat. Nos. 4,027,393 ; 4,569,673. A modification of the method is taught in U.S. Pat. No. 4,126,937. In the invention described in this patent, which is a method of treating dental pulp infection, dental cap material comprising silver particles is placed into a cavity prepared in a dental restoration procedure. The dental cap material acts as one electrode, a silver wire is placed into the dental cap material to enable a direct current power source to be connected, a second contact is provided on the patient to complete the circuit and a direct current is applied for a period of about ten minutes. The current source is then removed and the inventor claims that the silver ion activity continues at a decreasing rate for a few hours and indefinitely at a very low level.

electrically liberated silver ions by iontophoresis; Electrochemical principles form the basis for many applications routinely used in medicine today. For example, U.S. Pat. No. 5,814,094 teaches a iontophoretic system for promoting tissue healing processes and inducing regeneration. The system includes a device a method for using it, a composition, and methods for making the composition in vitro and in vivo. The system is implemented by placing a flexible, silver-containing anode in contact with the wound, placing a cathode on intact skin near the anode, and applying a wound-specific DC voltage between the anode and the cathode. Electrically-generated silver ions from the anode penetrate into the adjacent tissues and undergo a sequence of reactions leading to formation of a silver-collagen complex. This complex acts as a biological inducer to cause the formation in vivo of an adequate blastema to support regeneration.

Iontophoresis without an external current source; U.S. Pat. No. 5,322,520 teaches an electrode arrangement made up of particles or layers of two different metals that are separated by a resistive material. The electrode arrangement is incorporated into or attached to medical devices, e.g. catheters. When surrounded by and in contact with an electrolytic fluid, i.e. body fluids, galvanic current flows between the two metals and metal ions are released into the fluid.

SUMMARY OF THE INVENTION

According to at least some embodiments of the present invention, there is provided a system featuring two electrodes made of two different metals having a potential difference between them which are implanted in the body, to enable ions of the active electrode to be released to the body in a continuous current and in a local centered fashion. In one embodiment the active electrode is made of metallic silver and is implanted in the bone. After implantation of the electrodes and current induction a very low continuous current of silver ions is maintained in the bone for an extended period of time. Without wishing to be limited by a single hypothesis, the silver implant device is estimated to confer a clinical benefit in cases of bone infections (Osteomyelitis), by reducing the infection in the bone area, in the vicinity of the implanted active electrode. According to other embodiments of the present invention, there is provided a treatment method and apparatus for manually installing the two electrodes and initiating the current flow.

According to still other embodiments of the present invention, there is provided an apparatus that may optionally be used to manually, semi-automatically, or fully automatically install the electrodes of an implantable battery stably in the body of a patient by a minimal invasive procedure.

According to yet other embodiments of the present invention, there is provided an apparatus that allows monitoring and control of the flow of ions from the active electrode during the lifetime of the battery.

According to other embodiments of the present invention, there is provided an apparatus for activating and operating an implantable battery inside a human or animal body. The apparatus comprises:

(a) At least two electrodes adapted to be implanted in the body. The electrodes include at least one active electrode composed of a metallic material and at least one passive electrode composed of a material whose electrical potential is negative relative to the electrical potential of the active electrode; and i. A power source for application of current to the at least one active electrode to cause release of metallic ions from the active electrode; and ii. A control unit for automatically controlling the output of the power source in order to control the release of the metallic ions.

The active electrode can comprise one of the following: silver, iron, zinc, or magnesium. In an embodiment of the apparatus of the invention the control unit and the power source are external to the body. In other embodiments the control unit and the power source are adapted for implantation in one or more of the following locations inside the body: subcutaneously, muscle, fat, hard tissue, bone, and cartilage.

The control unit initiates an initial application of current by the power source for one or more limited periods of time and thereafter the metallic ions continue to be released from the active electrode after the limited periods of time. In embodiments of the apparatus of the invention, the level of current applied to the active electrode is determined by the type of tissue into which the active electrode is implanted and the type of pathology of the tissue and the electrical properties of the electrodes.

The active electrode may optionally be a pin made of metallic silver which is stably implanted in a bone in which case the passive electrode can function as an accessory, which facilitates a very slow release of silver ions from the silver pin to maintain a long term bactericidal effect around the silver pin thereby allowing the silver pin to serve the mechanical function of acting as an antibacterial protected fiducial marker.

According to still other embodiments of the present invention, the control unit comprises one or more of the following components:

a resistance meter adapted to measure the resistance between the active and the passive electrodes and/or to measure the resistance between the active electrode and a body site in order to determine the location of the passive electrode;

a voltmeter adapted to measure the voltage difference between the active and the passive electrodes;

a processor adapted to control the supply of applied current by comparing measured values of the metallic ion current from the active electrode to a pre-set threshold and activating the power source to increase the release of ions if the measured metallic ion current is lower than the threshold;

a memory component to store the data recorded and/or measured by the components of the control unit;

a transmitter/receiver component for communication with a remote processing and display subsystem; and a housing containing all the components of the controller.

The power source may optionally be located within the housing of the control unit and the power source adapted to supply a starting or maintenance current to release ions from the active electrode and to supply electrical power to other components of the control unit. The power source is adapted to supply DC power, or AC power, or both and is also adapted to supply the power at various frequencies and having various waveforms. The waveforms may optionally be, for example, sinusoidal, triangular, or square. Embodiments of the power can supply electric current, an electrical potential difference, or both. Embodiments of the A.C. power source include components that are adapted to scan a range of frequencies to find the frequency that provides the best ratio of voltage to metallic ion current.

Embodiments of the control unit are adapted to be implanted in the body and have a rounded form and small dimensions, with a diameter less than 2.5 cm and thickness less than 3 mm. Embodiments of the implantable control unit have a projection having threads on its outer surface on the bottom center of the housing, thereby allowing the control unit to be attached to hard tissue. In these embodiments the passive electrode may optionally be created on the surface of the housing by coating a part of the surface with a layer of the metallic material of the passive electrode and the remainder of the surface may optionally be coated with an electrically insulating material, thereby eliminating the need for a separate passive electrode.

In embodiments of the control unit that are implanted subcutaneously, the passive electrode may optionally be created on the surface of the housing by coating a part of the surface with a layer of the metallic material of the passive electrode and the remainder of the surface is coated with an electrically insulating material, thereby eliminating the need for a separate passive electrode.

Embodiments of the remote processing and display subsystem comprise a monitor, input/output device, and software. The remote processing and display subsystem may optionally be a PC or a laptop computer or a hand-held digital device adapted to function as a user interface with the controller.

Embodiments of the remote processing and display subsystem are designed to enable some or all of the following functions for controlling, storing, analyzing and displaying data:
  displaying the present and historical instantaneous values of the active ion current;
  displaying the accumulative value of the active ion current recorded from the beginning of operation or between selected starting and end times;
  pre-selection for automatic display or manual setting of the time slot for displaying the data;
  statistical analysis and display of the recorded and derived parameters;
  displaying and changing the current value of the threshold;
  displaying the status of the internal battery; and
  displaying a message announcing that the ion current has stopped.

The derived parameters that are displayed may optionally be one or more of: electrical charge, amount of material of the active electrode used, amount of material of the active electrode remaining, estimated remaining lifetime of the active electrode, maximum ion current recorded, mean value of the current, mean value of the current over a pre-defined time period.

According to other embodiments of the present invention, there is provided an apparatus for implanting an active electrode in hard tissue. The apparatus comprises:
  i. a rigid base plate and a rigid platform that are connected by an axle and a rotation mechanism such that the platform may optionally be rotated around the axis relative to the plate;
  ii. a trocar rigidly attached to and projecting downward from the bottom of the base plate;
  iii. optionally, straps or another type of arrangement attached to the base plate to stabilize the apparatus prevent it from moving during the process of implanting the active electrode;
  iv. two vertical holes bored through the rigid platform, wherein the holes are located on the platform such that, when the platform is rotated around a vertical axis passing through the axle the holes may optionally be brought to a position in which they are co-axial with a channel in the center of the trocar;
  v. two hollow vertical posts rigidly attached to the top surface of the platform such that the channel through each of them is coaxial with the holes respectively;
  vi. a shaft, which passes through the first of the posts, wherein the distal end of the shaft is either a hardened pointed to form an orthopedic punch or has spiral grooves machined into it forming a drill tip, wherein the shaft is used to create a hole in the hard tissue into which the active electrode is implanted; and
  vii. a pusher which passes through the second of the posts; wherein the active electrode is located at the distal end of the pusher.

In embodiments of the apparatus of the invention, the diameter of the hole that is created in the hard tissue and the diameter of active electrode are related to each other such that, when the electrode is inserted into the hole, the hard tissue will push against the sides of the electrode, holding it in place even before the tissue begins to re-grow around the electrode.

In embodiments of the apparatus of the invention, mechanical and electrical contact between each of the active and passive electrodes and an electrically conducting wires may optionally be achieved by creating a contact surface on an end of the electrode and creating a matching contact surface on the end of the conducting wire, positioning the contact surfaces adjacent to each other, and sliding a tight fitting sheath of insulating material over the contact surfaces at the end of the wire and the electrode thereby pressing the matching contact surfaces together. The mechanical and electrical contact between each of the active and passive electrodes and the conducting wires may optionally be broken by pulling the tight fitting sheath of insulating material back from the contact surfaces at the end of the wire and the electrode thereby uncovering the matching contact surfaces.

In embodiments of the apparatus of the invention the diameter of a part of the hole that is created in the hard tissue and the diameter of the sheath of insulating material are related to each other such that, when the sheath of insulating material is inserted into the hole, the hard tissue will push against the sides of the sheath of insulating material holding it in place. A clamp may optionally be used to pull the sheath of insulating material proximally relative to the conducting wire, thereby uncovering the connection between the electrode and the wire whereby the wire may optionally be disconnected from the electrode allowing the wire and sheath to be withdrawn from the body leaving the active electrode embedded in the hard tissue.

In embodiments of the apparatus of the invention, the dimensions of the apparatus are determined from the volume of active electrode material needed to achieve the desired release of ions for the desired period of time and the depth of the implant location in the hard tissue and the thickness of the overlaying muscle/fat layers of the patient at that location.

Embodiments of the apparatus of the invention may optionally be activated in one of the following ways: manually, semi-automatically, or fully automatically. If the apparatus is either activated semi-automatically or fully automatic it can comprise a source of electric power, an electric control circuit, a controller, sensors, and one or more electric motors. If the apparatus is activated fully automatically it can comprise a housing having operating buttons and signal lights on its outer surface for initiating the different operations of the apparatus that encloses all of the components of the apparatus. The apparatus may optionally be designed and used only for one procedure.

According to other embodiments of the present invention, there is provided a device for implanting a passive electrode subcutaneously. The device comprises:
  i. a base plate having a vertical hole bored through it;
  ii. optionally, straps or another type of arrangement attached to the base plate to stabilize the apparatus preventing it from moving during the process of implanting the active electrode;
  iii. a trocar rigidly attached coaxially with the hole to the lower surface of the base plate;
  iv. a hollow post rigidly attached coaxially with the hole to the upper surface of the base plate;
  v. a pusher, which passes through the post, wherein the active electrode is located at the distal end of the pusher.

Embodiments of the apparatus of the invention may optionally be activated in one of the following ways: manually, semi-automatically, or fully automatically. If the device is either activated semi-automatically or fully automatically it can comprise a source of electric power, an electric control circuit, a controller, sensors, and one or more electric motors. The device may optionally be designed and used only for one procedure.

According to other embodiments of the present invention, there is provided a method of using the apparatus as described herein for implanting an active electrode in hard tissue. The method comprises:
  (a) determining the location at which the electrode is to be implanted;
  (b) positioning the trocar above the location;
  (c) pressing the apparatus against the skin until the trocar penetrates the skin and muscle/fat layer;
  (d) optionally attaching the apparatus in place;
  (e) rotating the rigid platform until the first of the posts is aligned with the trocar;
  (f) lowering the shaft until its distal end contacts the hard tissue;
  (g) rotating the shaft 42, thereby advancing the distal end into and creating a hole in the hard tissue;
  (h) rotating the shaft in the opposite direction to remove the distal end from the hard tissue;
  (i) raising the shaft until it is returned to its original position;
  (j rotating the rigid platform until the second post is aligned with the trocar
  (k) lowering the pusher until the active electrode is pushed into the hole that was created in the hard tissue;
  (l) raising the pusher until it is returned to its original position; and
  (m) removing the apparatus from the skin.

According to other embodiments of the present invention, there is provided a method of using the device for implanting a passive electrode subcutaneously. The method comprises:
  (a) pushing the base plate the surface of the skin until the trocar penetrates the soft tissue;
  (b) optionally attaching the device in place;
  (c) pushing the pusher downward injecting the passive electrode into the soft tissue;
  (d) tilting the device such that the passive electrode is embedded subcutaneously roughly parallel to the skin surface;
  (e) removing the device from the skin.

According to other embodiments of the present invention, there is provided a method of treatment and prevention of infectious diseases. The method comprises:
  a. using the method as described above to implant a silver electrode at the location of the actual or potential infection;
  b. connecting electrically the silver electrode with a first terminal of a resistance meter;
  c. connecting electrically a needle made from a biocompatible material having the same electrical potential or a negative electrical potential with respect to silver to a second terminal of the resistance meter;
  d. touching the skin with the needle at a spot near the silver electrode and measuring the resistance of the path from the silver electrode to the needle;
  e. repeating step d at different locations until the path having the lowest resistance is found and marking the corresponding location of the needle;
  f. repeating steps d and e to locate one or more additional corresponding locations, if desired;
  g. disconnecting the resistance meter from the silver electrode and removing the resistance meter and the needle;
  h. using the method as described above to implant a passive electrode made from the biocompatible material subcutaneously at each of the corresponding locations;
  i. connecting electrically one terminal of an electrical power source to the silver electrode and the second terminal of the current source to a first one of the passive electrodes, thereby initiating the release of silver ions by applying a small current between the silver electrode and the first one of the passive electrodes;
  j. disconnecting the second terminal of the power source from the first one of the passive electrodes;
  k. repeating steps i and j for each of the other passive electrodes.

Some or all of steps b to g and i to k of the method may optionally be carried out using the apparatus of the invention.

According to other embodiments of the present invention, there is provided a system for implanting, activating, and operating an implantable battery inside a human or animal body to cure a wide range of pathologies. The system comprises at least one of each device and apparatus as described herein. The pathologies may optionally be selected from: osteomyelitis, chronic osteomyelitis, bone infections caused by diabetes, infectious arthritis, rheumatoid arthritis, psoriasis, and lupus, osteoporosis, non-union, and delayed union. The system may optionally be used to promote bone healing, bone growth, and bone strengthening.

According to other embodiments of the present invention, there is provided an apparatus for activating and operating an implantable battery inside a human or animal body, said apparatus comprising:
  at least two electrodes adapted to be implanted in said body, said electrodes including at least one active electrode composed of a metallic material and at least one passive electrode composed of a material whose electrical potential is negative relative to the electrical potential of said active electrode; and
  one or more of the following:
    a power source for application of current to the at least one active electrode to cause release of metallic ions from said active electrode; and a control unit for automatically controlling the output of said power source in order to control the release of said metallic ions.

Optionally the active electrode comprises one of the following: silver, iron, zinc, or magnesium.

Optionally the active electrode is made of silver or a silver alloy and the passive electrode is made of gold or platinum.

Optionally the active electrode is made of iron, zinc, or magnesium and the passive electrode is made of gold.

Optionally the control unit and the power source are external to the body.

Optionally the control unit and the power source are adapted for implantation in one or more of the following locations inside the body: subcutaneously, muscle, fat, hard tissue, bone, and cartilage.

Optionally the control unit initiates an initial application of current by the power source for one or more limited periods of time and wherein the metallic ions continue to be released from the active electrode after said limited periods of time.

Optionally the level of current applied to the active electrode is determined by the type of tissue into which the active electrode is implanted and the type of pathology of said tissue and the electrical properties of the electrodes.

Optionally the active electrode is a pin made of metallic silver which is stably implanted in a bone and the passive electrode functions as an accessory, which facilitates a very slow release of silver ions from said silver pin to maintain a long term bactericidal effect around said silver pin thereby allowing said silver pin to serve the mechanical function of acting as an antibacterial protected fiducial marker.

Optionally the control unit comprises one or more of the following components:

a resistance meter adapted to measure the resistance between the active and the passive electrodes and/or to measure the resistance between said active electrode and a body site in order to determine the location of said passive electrode;

a voltmeter adapted to measure the voltage difference between said active and said passive electrodes;

a processor adapted to control the supply of applied current by comparing measured values of the metallic ion current from said active electrode to a pre-set threshold and activating the power source to increase the release of ions if said measured metallic ion current is lower than said threshold;

a memory component to store the data recorded and/or measured by the components of said control unit;

a transmitter/receiver component for communication with a remote processing and display subsystem; and a housing containing all the components of said controller.

Optionally the power source is located within the housing of the control unit and said power source is adapted to supply a starting or maintenance current to release ions from the active electrode and to supply electrical power to other components of the control unit.

Optionally the power source is adapted to supply DC power, or AC power, or both and is also adapted to supply said power at various frequencies and having various waveforms.

Optionally the waveforms are chosen from: sinusoidal, triangular, and square.

Optionally the power can supply electric current, an electrical potential difference, or both.

Optionally the A.C. power source comprises components that are adapted to scan a range of frequencies to find the frequency that provides the best ratio of voltage to metallic ion current.

Optionally the control unit is adapted to be implanted in the body and has a rounded form and small dimensions, with a diameter less than 2.5 cm and thickness less than 3 mm.

Optionally the bottom center of the housing of the control unit comprises a projection having threads on its outer surface, thereby allowing said control unit to be attached to hard tissue.

Optionally the passive electrode is created on the surface of the housing by coating a part of said surface with a layer of the metallic material of said passive electrode and the remainder of said surface is coated with an electrically insulating material, thereby eliminating the need for a separate passive electrode.

Optionally the control unit is implanted subcutaneously and the passive electrode is created on the surface of the housing by coating a part of said surface with a layer of the metallic material of said passive electrode and the remainder of said surface is coated with an electrically insulating material, thereby eliminating the need for a separate passive electrode.

Optionally the remote processing and display subsystem comprises a monitor, input/output device, and software; for example a PC or a laptop computer or a hand-held digital device adapted to function as a user interface with the controller.

Optionally the remote processing and display subsystem is designed to enable some or all of the following functions for controlling, storing, analyzing and displaying data:

displaying the present and historical instantaneous values of the active ion current;

displaying the accumulative value of said active ion current recorded from the beginning of operation or between selected starting and end times;

pre-selection for automatic display or manual setting of the time slot for displaying the data;

statistical analysis and display of the recorded and derived parameters;

displaying and changing the current value of the threshold;

displaying the status of the internal battery; and displaying a message announcing that said ion current has stopped.

Optionally the derived parameters that are displayed are one or more of: electrical charge, amount of material of the active electrode used, amount of material of said active electrode remaining, estimated remaining lifetime of said active electrode, maximum ion current recorded, mean value of said current, mean value of said current over a pre-defined time period.

According to other embodiments of the present invention there is provided an apparatus for implanting an active electrode in hard tissue, said apparatus comprised of:

a rigid base plate and a rigid platform that are connected by an axle and a rotation mechanism such that said platform can be rotated around said axis relative to said plate;

a trocar rigidly attached to and projecting downward from the bottom of said base plate;

optionally, straps or another type of arrangement attached to said base plate to stabilize said apparatus prevent it from moving during the process of implanting said active electrode;

two vertical holes bored through said rigid platform, wherein said holes are located on said platform such that, when said platform is rotated around a vertical axis passing through said axle said holes can be brought to a position in which they are co-axial with a channel in the center of said trocar;

two hollow vertical posts rigidly attached to the top surface of said platform such that the channel through each of them is coaxial with said holes respectively;

a shaft, which passes through the first of said posts, wherein the distal end of said shaft is either a hardened pointed to form an orthopedic punch or has spiral grooves machined into it forming a drill tip, wherein said shaft is used to create a hole in said hard tissue into which said active electrode is implanted; and a pusher which passes through the second of said posts; wherein said active electrode is located at the distal end of said pusher.

Optionally the diameter of the hole that is created in the hard tissue and the diameter of active electrode are related to each other such that, when said electrode is inserted into said hole, said hard tissue will push against the sides of said electrode, holding it in place even before said tissue begins to re-grow around said electrode.

Optionally mechanical and electrical contact between each of the active and passive electrodes and an electrically conducting wires is achieved by creating a contact surface on an end of said electrode and creating a matching contact surface on the end of said conducting wire, positioning said contact surfaces adjacent to each other, and sliding a tight fitting sheath of insulating material over said contact surfaces at the end of said wire and said electrode thereby pressing said matching contact surfaces together.

According to other embodiments of the present invention, there is provided a device for implanting a passive electrode subcutaneously, said device comprised of:

a base plate having a vertical hole bored through it;

optionally, straps or another type of arrangement attached to said base plate to stabilize said apparatus preventing it from moving during the process of implanting said active electrode;

a trocar rigidly attached coaxially with said hole to the lower surface of said base plate;

a hollow post rigidly attached coaxially with said hole to the upper surface of said base plate;

a pusher, which passes through said post, wherein said active electrode is located at the distal end of said pusher.

Optionally said device for implanting a passive electrode can each be activated in one of the following ways: manually, semi-automatically, or fully automatically.

Optionally said device is either activated semi-automatically or fully automatically and comprises a source of electric power, an electric control circuit, a controller, sensors, and one or more electric motors.

Optionally said device is designed and used only for one procedure

According to some embodiments of the present invention, there is provided an apparatus for treatment and prevention of infectious diseases in a hard tissue surrounded by at least a portion of a soft tissue, said apparatus comprising:

a. a trocar for insertion to said soft tissue and said hard tissue and for creating an opening in said soft tissue and said hard tissue;

b. a punch for insertion through said opening in said soft tissue and said hard tissue, and for deepening said opening in said hard tissue;

c. a pusher;

d. a silver electrode for entering said opening in soft tissue and said opening in said hard tissue through pushing by said pusher;

e. a temporary electrode for entering said opening in soft tissue and said opening in said hard tissue through pushing by said pusher on top of said silver electrode;

f. a needle made from a biocompatible substance having a negative electrical potential with respect to silver;

g. one or more second electrodes made from the same material as said needle for insertion through said soft tissue at a location separated from said opening in said soft tissue; and h. a conductivity meter attached to said needle;

Wherein upon contacting said needle to said soft tissue, said conductivity meter provides a reading for determining said location for said one or more second electrodes.

Optionally the apparatus comprises an external D. C. voltage source.

Optionally the disease is a bacterial infection following an orthopedic procedure, such as osteomyelitis or chronic osteomyelitis.

Optionally the disease is infectious arthritis or a rheumatic malady.

Optionally the silver electrode comprises pure silver or the silver electrode comprises a combination of pure silver and a percentage of the material used to make the second electrode.

Optionally the silver electrode weighs between 1 mg and 50 mg.

Optionally the needle and the second electrode are made from gold.

Optionally the second electrode weighs between 5 mg and 100 mg.

Optionally the temporary electrode comprises a small metallic cylinder surrounded on all but its bottom surface by an electrically insulating layer and connected to a long insulated electricity conducting wire.

According to some embodiments of the present invention, there is provided a method of treatment and prevention of infectious diseases, said method comprising the stages of boring a hole into a bone or a joint; implanting a small silver electrode into said hole; placing a temporary electrode in said hole, on top of and in intimate contact with said silver electrode; connecting electrically said temporary electrode with a first terminal of a conductivity meter; connecting electrically a needle made from a biocompatible substance having a negative electrical potential with respect to silver to a second terminal of said conductivity meter; touching the skin with said needle at a location near said hole and measuring the conductivity of the path from said silver electrode to said needle; repeating said touching the skin with said needle at different locations until the path having the highest conductivity is found and marking the corresponding location of said needle; repeating said touching the skin with said needle at least once more to locate one or more additional corresponding locations, if desired; disconnecting said conductivity meter from said temporary electrode and removing said conductivity meter and said needle; embedding a second small electrode made from said biocompatible material subcutaneously at each of said corresponding locations; connecting electrically one terminal of a D. C. voltage source to the temporary electrode and the second terminal of said D. C. voltage source to a first one of said second electrodes, thereby initiating the release of silver ions by applying a small current between said silver electrode and said first one of said second electrodes; disconnecting said second terminal of said D. C. voltage source from said first one of said second electrodes; repeating said connecting electrically one terminal of a D. C. voltage source to the temporary electrode and said disconnecting said second terminal for each of said other second electrodes; and removing said temporary electrode and said D. C. voltage source.

The power source may also optionally comprise an AC voltage source.

Optionally the hole is bored into the infected area of the bone or in the vicinity of the infected area of the bone.

Optionally the needle and the second electrode are made from gold.

Optionally the second electrode weighs between 5 mg and 100 mg.

Optionally the temporary electrode is comprised of a small metallic cylinder surrounded on all but its bottom surface by an electrically insulating layer and connected to a long insulated electricity conducting wire.

Optionally the D. C. voltage source delivers a current of less than 0.5 mA to initiate the release of silver ions.

Optionally the D. C. voltage source delivers a current for between 5 seconds and 120 seconds to initiate the release of silver ions.

All the above and other characteristics and advantages of the invention will be further understood through the following illustrative and non-limitative description of preferred embodiments thereof, with reference to the appended drawings.

BRIEF DESCRIPTION OF THE DRAWINGS

FIGS. 10A to 10H schematically show the components of the apparatus of the invention; and FIGS. 11 to 19 schematically illustrate the steps of the method of the invention.

DETAILED DESCRIPTION

Figure 1:
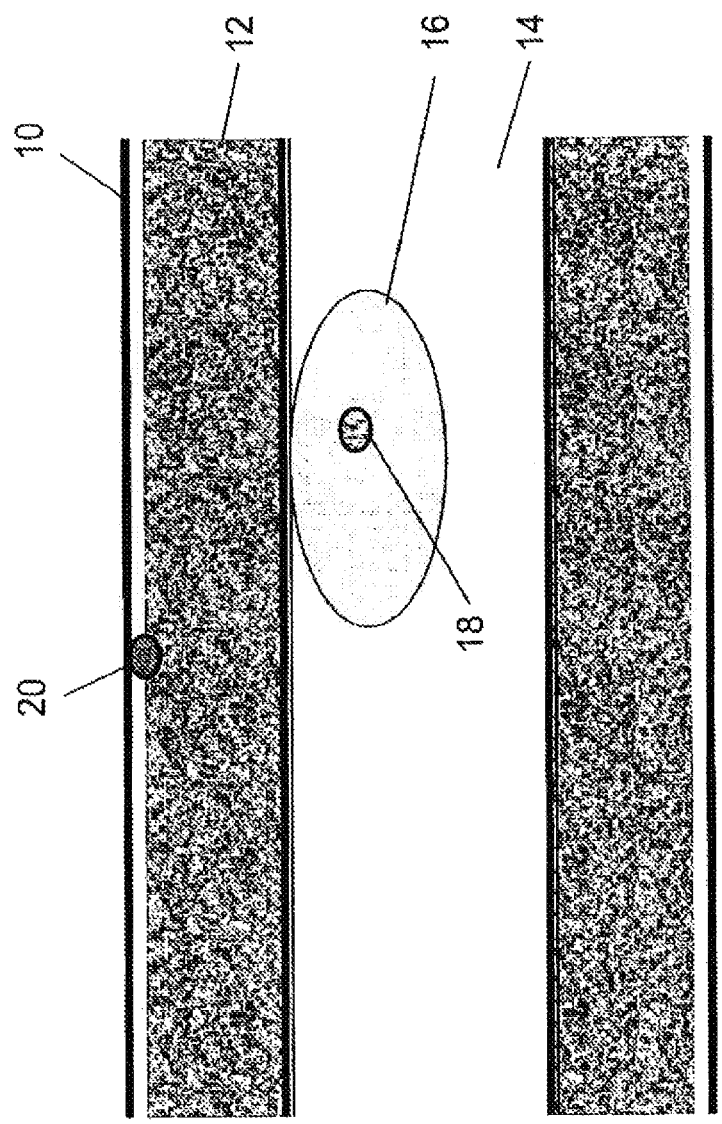
FIGS. 1 to 3 schematically show the physical principle of operation of the invention.

The present invention is apparatus, systems, and methods for the treatment of bone, cartilage and other types of hard tissue. The treatments, which are suitable for extended treatment, include the treatment and prevention of pathologies through the controllable use of silver, iron, zinc, or magnesium ions. These pathologies may include a pathology which is at least partially induced or aggravated by an infectious disease, for example a bacterial disease. In this case the electrically released ions are silver ions, which are known to have antibacterial properties.

The devices, system, and method may optionally be used to cure a wide range of pathologies, e.g. osteomyelitis; chronic osteomyelitis; other types of bone infections such as caused by diabetes; infectious arthritis; certain kinds of rheumatic maladies, e.g. rheumatoid arthritis, psoriasis, and lupus; osteoporosis; non-union, delayed union, and promote bone healing and bone growth/strengthening. The invention will be illustrated herein mainly in terms of the use of silver ions for the treatment of chronic osteomyelitis, however the invention is not specifically limited to treatment of this disease and skilled persons will be able to adapt the method and apparatus described herein mutatis mutandis for the treatment of other diseases.

Embodiments of the system of the present invention comprise a control unit that is electrically connected to at least one active and at least one passive electrode. The active electrode(s) comprise a material that is capable of releasing ions of silver, iron, zinc, or magnesium upon application of electrical energy to the electrodes. The passive electrode(s) comprises a type of metallic material having an electric potential that is negative relative to the potential of the active electrode, thereby allowing an ion current to continue to flow once an external source of electrical energy is withdrawn. Such arrangement will allow any two metallic materials or alloys to form an electrophysiological battery, provided there is a suitable potential difference between the two materials and the ions of the active electrode are needed for a medical purpose. The electrodes are inserted into the tissue to be treated. The electrodes and control unit, together with the tissue between them, comprise a closed series electrical circuit through which either an externally imposed or galvanic current can flow. Embodiments of the control unit enable automatic control of the release of ions from the active electrode to be controlled by application of electrical energy to the electrodes.

Embodiments of the control unit optionally comprise a power source used to supply a starting or maintenance current to release silver ions from the active electrode(s) and to supply electrical power to other components of the control unit. The current supplied for the initiation phase may optionally be either DC or AC current, at various frequencies and having various waveforms, for example sinus, triangle, square, etc. The control unit can optionally be operated by a single use, replaceable, or rechargeable battery.

Embodiments of the control unit optionally comprise one or more of the following:

A resistance meter, to measure the resistance between the active and passive electrodes and/or to measure the resistance between the active electrode and a body site in order to determine the location of the passive electrode.

A voltmeter, to measure the voltage difference between the two electrodes. This measurement together with the resistance measurement will allow the value of the current (galvanic or applied) to be determined.

A processor to control the supply of applied current. The processor functions in a closed loop. The value of the ion current from the active electrode may optionally be measured either continuously or periodically and compared to a pre-set threshold. If the current is lower than the threshold the power source will be activated to increase the release of ions until a value of the ion current higher than the threshold is obtained. If the measured value of the ion current is above the threshold, the power source will not be activated.

A memory component, for storing data, e.g. the current values of the ion current that are measured are recorded and stored in a data base.

A transmitter/receiver component for communication with a remote processing and display subsystem, preferably by RF, magnetic, WiFi, or other known wireless technology.

The system of the invention as described herein preferably also comprises a remote processing and display subsystem comprising a monitor, input/output device, and software, e.g. a computer of some type or a hand-held digital device, which functions as a user interface with the controller. The remote subsystem is designed to enable many different functions for controlling, storing, analyzing and displaying data. Illustrative examples of some of these functions are:

- display of the present and historical instantaneous values of the active ion current;
- display of the accumulative value of the active ion current recorded from the beginning of operation or between selected starting and end dates and times;
- pre-selection for automatic display or manual setting of the time slot for displaying the data;
- statistical analysis and display of the recorded and derived parameters, e.g. electrical charge, amount of silver used, amount of silver remaining, estimated remaining lifetime of the active electrode, maximum current recorded, mean value of the current, mean value over a defined time period;
- displaying and changing the value of the current threshold;
- display of the status of the internal battery; and
- display of a message announcing that the ion current has stopped.

The control unit may optionally be either an external unit or may optionally be implanted in the body of the patient. An external control unit is preferably used for control purposes for a restricted period, for example for 24 or 48 hours, to allow current monitoring to assure the battery is functioning as planned and the ionic current is above the predetermined threshold value. In an implanted control unit the current control functionality may optionally be used for a long period, for example more than a year. The implanted control unit may optionally be removed from the body of the patient by a minimal surgery at the physician's discretion.

Embodiments of the control unit that are to be implanted in the body preferably have a rounded form, non sharp edges, and small dimensions, e.g. diameter less than 2.5 cm and thickness less than 3 mm.

The implanted control unit may optionally be fixed to the bone or implanted subcutaneously, or inserted into some other type of tissue, including without limitation any type of hard tissue or cartilage, muscle or fat. The implanted control unit remains inside the body until the active electrode ceases to function, i.e. degrades and stops to release ions. Then the control unit may optionally be removed from the body, at physician discretion, preferably by a minimally invasive surgical procedure.

Embodiments of the method of the present invention for treatment of chronic osteomyelitis include the implantation of a battery comprising an active electrode including silver implanted in the infected bone and a passive electrode including another metallic element implanted subcutaneously and initiating the release of silver ions by applying a small current between the two electrodes. The initiation current is applied for a short time and then discontinued. The object of this initial current is to boost the ion release, for a stronger effect at treatment initiation. After this a continuous release of the silver ions will take place for a long time, which is estimated theoretically (but without wishing to be limited by a single hypothesis) to be more than one year, while spreading the silver ions to the surrounding tissue as well. This process assures a long-term antibacterial effect, which after accomplishing the infection healing will also provide preventive care.

The first step of the method is to identify the proper place to implant the active electrode. For the treatment of chronic osteomyelitis the active electrode is preferably implanted within the infected area in the bone or in its vicinity. The infected area may optionally be determined by standard methods such as x-ray imaging, CT scanning, or MRI.

Once the location of the place within the bone at which the silver (active) electrode is to be implanted is determined the bone is prepared using the apparatus of the invention. The active electrode is then delivered to the desired location. A second (passive) electrode is implanted subcutaneously at a location that is determined, using the system of the invention, near the active electrode. Means for applying a low current are then connected between the two electrodes, activated, and after a short time disconnected.

Figure 2:
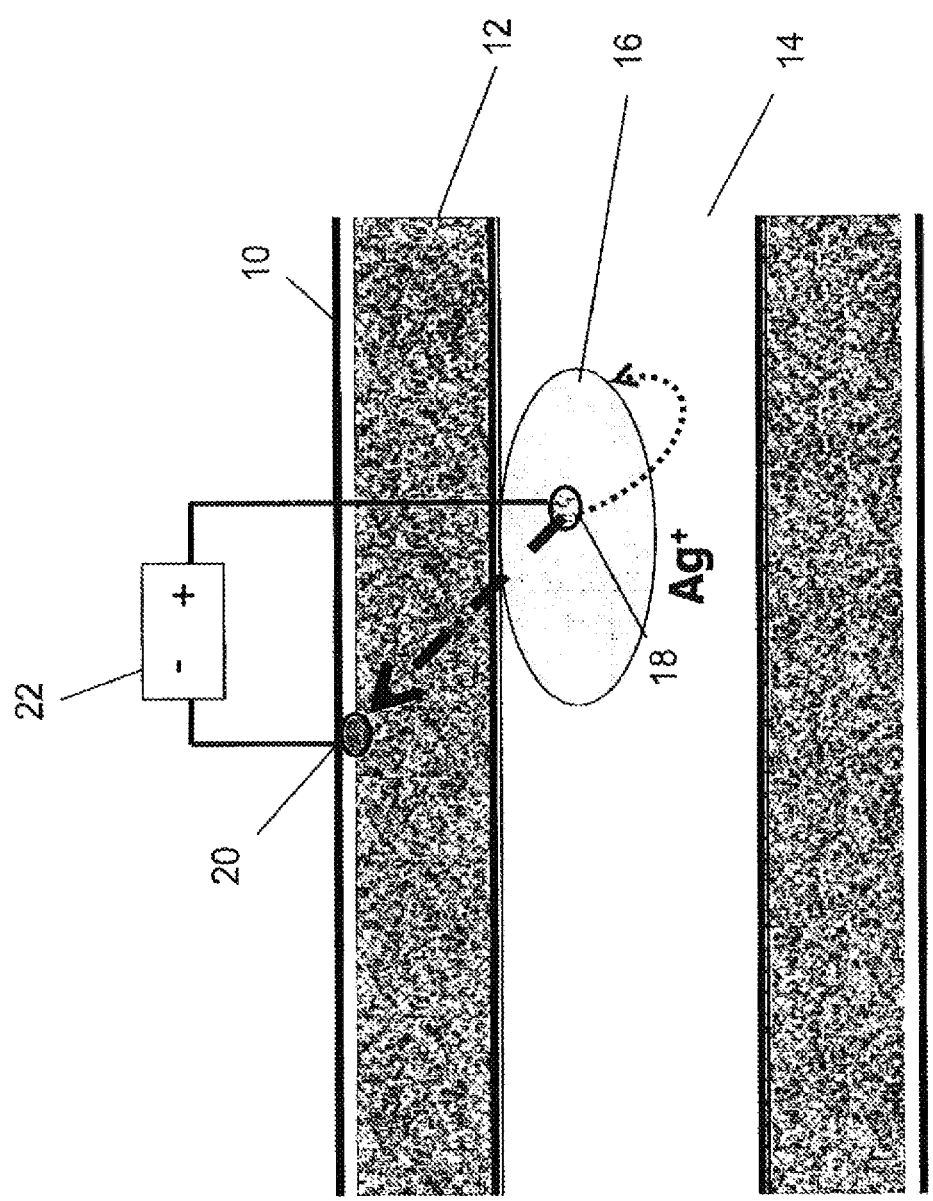
Figure 3:
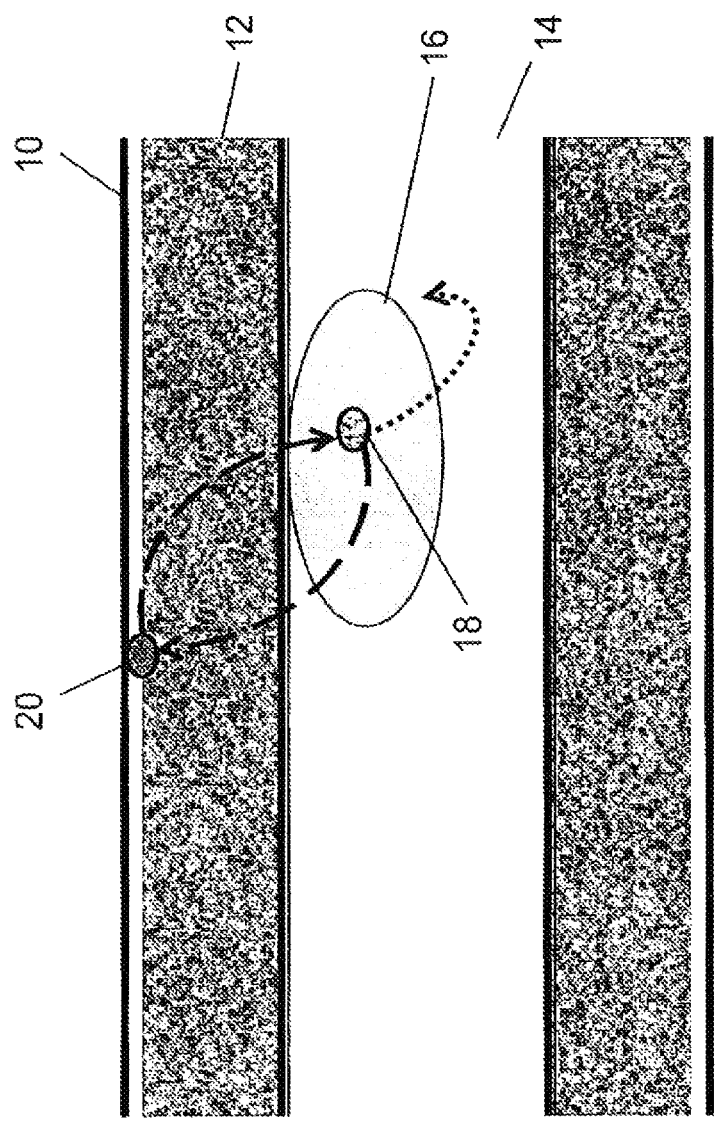

The physical principle of operation of the invention with regard to certain non-limiting embodiments is schematically shown in FIGS. 1 to 3. In FIG. 1 is shown the skin 10 and muscle/fat layers 12 surrounding bone 14. A silver electrode 18 is shown implanted in infected area 16 of bone 14. A second electrode 20 is shown implanted underneath the skin 10.

In FIG. 2 the positive side of external D.C. power source 22 is connected to the silver (active) electrode 18 and the negative side of power source 22 is connected to the second (passive) electrode 20. Alternatively an A.C. power source may optionally be used. In the A.C. case the power source may optionally be part of a device that is adapted to scan a range of frequencies to find the frequency that provides the best voltage-current ratio. Using either a D.C. or an A.C. power source, the bone and muscle/fat tissue conduct electricity and provide a path, shown symbolically by the straight dashed arrow, which completes the electric circuit. The current from power source 22 causes disintegration of silver electrode 18 by releasing silver ions, shown symbolically by the dotted arrow, into the infected area 16 from which they can slowly spread to other areas of the bone, surrounding tissue, and to more remote parts of the body. The level of current applied to the active electrode is determined by the resistance, which is dependent on the type of tissue into which the active electrode is implanted, the type of pathology of the tissue, and the electrical properties of the electrodes.

After the initialization of current flow the external power source 22 is disconnected from the electrodes. As shown in FIG. 3, the galvanic current continues to flow constituting what is essentially a galvanic battery comprising silver electrode 18 and second electrode 20 with an electrolyte comprised of the bone and tissue. This current will continue to flow releasing silver ions from silver electrode 18 as long as the two electrodes remain in place, i.e. until one or both of the electrodes 18, 20 is either physically removed, the silver (active) electrode totally disintegrates as a result of the prolonged flow of current, or the cathode (the passive electrode) becomes completely coated with silver.

The active and passive electrodes may optionally be implanted at any target site in the body, as required for a specific clinical purpose. They may optionally be made of any two biocompatible metals, materials or alloys, which have a suitable potential difference between them to form a battery, provided that the released ions have a clinical benefit. If the target site is an infected bone, then the active electrode is silver or a silver alloy and the clinical purpose is to reduce infection in bone infection cases by the antibacterial effect of the electrically released silver ions. In this case the passive electrode may optionally be gold, platinum or another biocompatible metal or alloy whose electrical potential is negative relative to the silver electrode. In another embodiment, the active (positive) electrode may optionally be made of iron, zinc, or magnesium and the passive (negative) electrode gold. In this case a possible application is to deliver zinc or magnesium to the bone in cases of osteoporosis.

Figure 4:
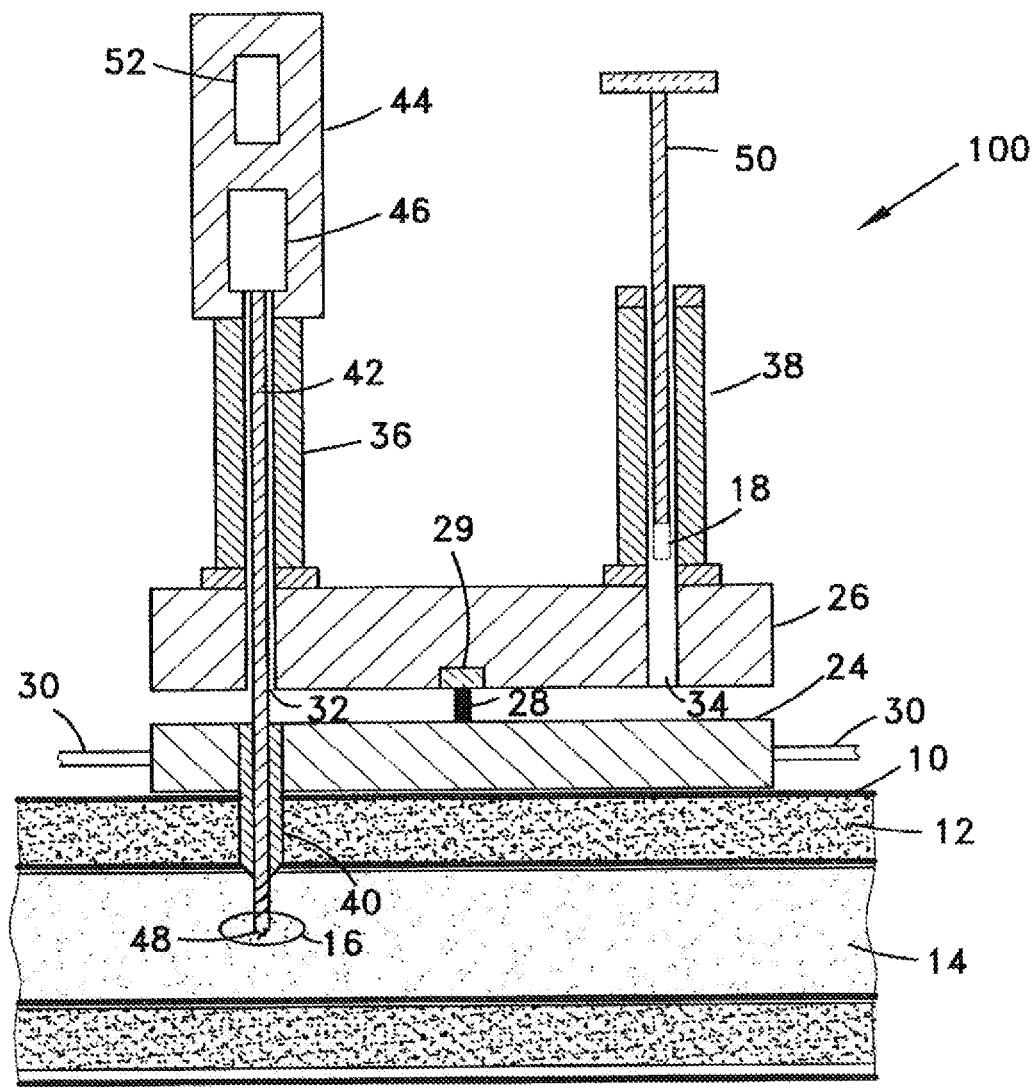
FIG. 4 schematically shows an apparatus 100 for embedding the active electrode 18 in hard tissue such as cartilage or a bone according to one embodiment of the invention.

FIG. 4 schematically shows components of an apparatus 100 for embedding the active electrode 18 in hard tissue such as cartilage or a bone according to an embodiment of the invention. Apparatus 100 is comprised of a rigid base plate 24 and a rigid platform 26 that are connected by an axle 28 and a rotation mechanism 29 such that platform 26 may optionally be rotated around axis 28 relative to plate 24.

Plate 24 has a trocar 40 rigidly attached to it and projecting downward from the bottom of apparatus 100. Apparatus 100 is positioned above the surface of the skin 10 such that the channel in the center of trocar 40 is directly inline with the location in the hard tissue at which the active electrode is to be installed, e.g. infected volume 18 of bone 14. Apparatus 100 is then pressed against the skin causing trocar 40 to penetrate the layers of skin 10 and muscle/fat 12 until the tip of trocar 40 reaches the surface of the bone 14. In some embodiments base plate 24 has straps 30 attached to it or another type of arrangement to stabilize apparatus 100 on the surface of the skin and to prevent it from moving during the process of installing the electrode.

Platform 26 has two vertical holes 32 and 34 bored through it. These holes are located on the platform such that, when platform 26 is rotated around a vertical axis passing through axle 28, they may optionally be brought to a position in which they are co-axial with the channel in the center of trocar 40. Hollow vertical posts 36 and 38 are rigidly attached to the top surface of platform 26 such that the channel through each of them is coaxial with holes 32 and 34 respectively.

Passing through post 36 is a shaft 42. The distal end 48 of shaft 42 can either be a hardened pointed to form an orthopedic punch or, as shown in FIG. 4, can have spiral grooves machined into it forming a drill tip. A handle 44 is attached to the proximal end of shaft 42. Shaft 42 may optionally be locked into an upper configuration in which the distal tip 48 does not pass through the bottom of platform 26. When aligned with trocar 40, shaft 42 may optionally be unlocked and lowered until the distal tip 48 penetrates the hard tissue to the depth at which the electrode is to be installed as shown in FIG. 4 and described herein below.

Passing through post 38 is pusher 50. At the distal end of pusher 50 is the active electrode 18, which is to be installed in bone 14. Not shown in the figure is the insulated conducting wire that is connected to electrode 18 and passes through a channel in pusher 50. Pusher 50 may optionally be locked into an upper configuration in which the electrode 18 does not pass through the bottom of platform 26 as shown in FIG. 4. When the platform is rotated until the pusher 50 is aligned with trocar 40, pusher 50 may optionally be unlocked and pushed downward until electrode 18 with the attached insulated conducting wire is installed in the hole in the hard tissue.

It is to be noted that none of the figures are drawn to even an approximate scale and that the scale varies from figure to figure. The actual sizes of the various components of the apparatus may optionally be determined by starting with the diameter of silver electrode 18, which is slightly less than the diameter of the bore created in the hard tissue, which is equal to the outer diameter of distal end 48 of shaft 42 and of pusher 50. The length of the trocar depends on the thickness of the muscle/fat layer overlaying the hard tissue at the location at which the electrode is to be implanted. The distance that the rod 42 and pusher 50 have to move up and down depend on the distance from the bottom of platform 26 to the bottom of the trocar plus the distance from the edge of the hard tissue to the bottom of the location at which the electrode is to be implanted. In designing an embodiment of apparatus 100 for a particular application or patient the main variables that must be taken into account are the volume of active electrode needed to achieve the desired release of ions for the desired period of time and the physical size of the patient, i.e. the depth of the implant location in the hard tissue and the thickness of the overlaying muscle/fat layers at that location. All dimensions of apparatus 100 can easily be determined from these parameters.

The procedure of delivering and implanting the active electrode 18 in hard tissue using apparatus 100 comprises the following steps:

(a) determining the location at which the electrode is to be implanted;
(b) positioning the trocar 40 above the location;
(c) pressing apparatus 100 against the skin until trocar 40 penetrates the skin and muscle/fat layer;
(d) optionally attaching apparatus 100 in place;
(e) rotate platform 26 until post 36 is aligned with the trocar 40;
(f) lowering shaft 42 until its distal end 48 contacts the hard tissue;
(g) rotating shaft 42 to advance the distal end into and creating a hole in the hard tissue;
(h) rotating shaft 42 in the opposite direction to remove the distal end from the hard tissue;
(i) raising shaft 42 until it is returned to its original position;
(j) rotating platform 26 until post 38 is aligned with the trocar 40;
(k) lowering pusher 50 until active electrode 18 is pushed into the hole that was created in the hard tissue;
(l) raising pusher 50 until it is returned to its original position;
(m) removing apparatus 100 from the skin.

Apparatus 100 may optionally be provided in several different embodiments. In a manual embodiment all steps (a) through (m) are carried out manually by the user. In a fully automatic embodiment of apparatus 100 all of the steps (e) through (l) are carried out automatically after the user activates a controller. Various embodiments allowing semi automatic operation are also possible, e.g. an embodiment in which steps (f) through (i) are carried out automatically and the remaining steps carried out manually or an embodiment in which only step (j) is carried out automatically.

The semi and fully automatic embodiments of apparatus 100 require a source of electric power, an electric control circuit, a controller, sensors, one or more electric motors, and various other electrical and mechanical components in order to perform the various steps of the procedure. All of these elements are well known in the art and may optionally be provided in many alternative forms therefore they will not be discussed in any great detail herein or shown in the figures. Electric power may optionally be supplied by an internal battery or connection to an external of AC or DC source supplying power and frequency appropriate for the other components of the apparatus. The controller may optionally be remote or located on the apparatus. For example, in FIG. 4 the controller is symbolically shown as 52 in handle 44. Controller 52 is a simple CPU preprogrammed to perform only the specific mechanical steps that are to be automatically carried out by the specific embodiment of apparatus 100. The electric circuit includes a button or switch to activate the controller and optionally lights or other indicators to signal that the automatic steps are being executed and optionally, which step. The mechanical components can include a reversible electric motor 46 to rotate shaft 42 causing it to be raised and lowered and also to create the bore in the hard tissue by pushing the punch into it or turning the drill. A similar reversible electric motor (not shown in the figure) may optionally be supplied to raise and lower pusher 50. Rotation mechanism 29 will comprise an electric motor in the fully automatic and some of the semi-automatic embodiments of apparatus 100. Optical or mechanical sensors are provided for example, to detect when the shaft 42 has been lowered to its maximum depth and to signal controller 52 to reverse the direction of motor 46, to signal controller 52 to shut off motor 46, when shaft 42 has been raised to its maximum height, and to activate and stop the motor in rotation mechanism 29 to change the position of shaft 42 and pusher 50 relative to trocar 40. In the fully automatic option, all of the components of apparatus 100 may optionally be enclosed within a housing having operating buttons and signal lights on its outer surface for initiating the different operations of the apparatus.

After the active electrode 18 connected to the insulated electrode wire has been inserted into the bore made in the hard tissue, apparatus 100 is removed leaving the electrode stably fixed in the hard tissue and the insulated electrode wire connected to it. Note that while the apparatus 100 may optionally be made to be reusable, in practice because the operating environment in which the procedure is carried out is normally so contaminated, the results of attempts to sterilize apparatus 100 after use can not be guaranteed and therefore it is recommended that apparatus 100 be designed and used only for one procedure.

Figure 5:
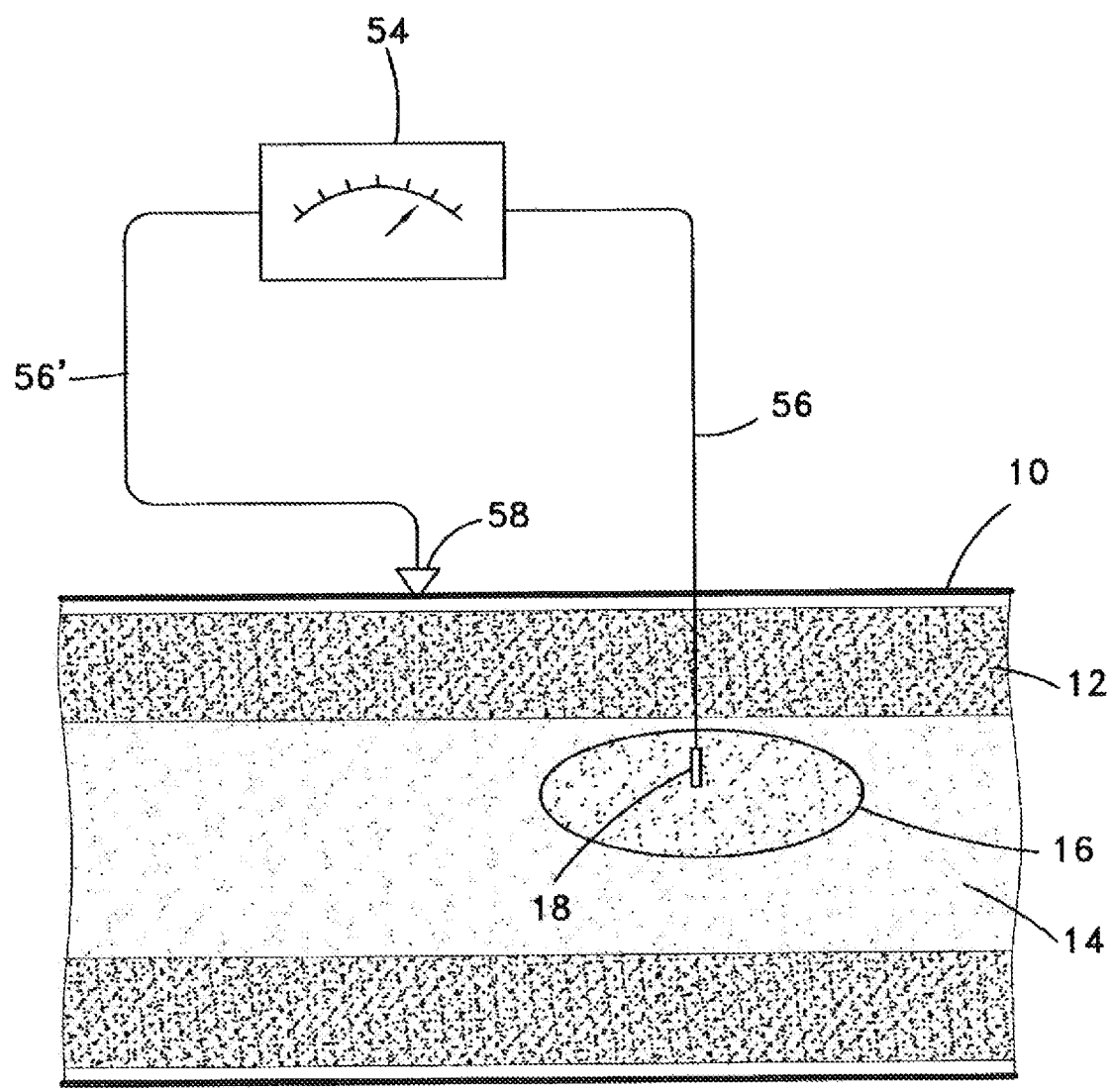
FIG. 5 schematically shows the method for locating the optimal position for placement of the passive electrode.

At this stage the location of the passive electrode is determined. According to the method described with regard to FIGS. 10-19 below, the most effective results will be obtained if the passive electrode is placed at the location under the surface of the skin at which the electrical resistance between the second electrode and the silver electrode is minimized. FIG. 5 schematically shows the method for locating the optimal position for placement of the passive electrode. One terminal of conductivity meter 54 is connected to the insulated electrically conducting wire 56 connected to active electrode 18, embedded in infected area 16 of bone 14. The other terminal of conductivity meter 54 is connected to electrically conducting wire 56', which has a needle 58 attached to its free end. Needle 58 is made of the same material as is the active electrode or from another biocompatible material having a negative electrical potential with respect to the material of the active electrode. When needle 58 touches the skin a closed circuit is set up and the meter reads the resistance of the circuit. If the needle is moved to a different location a different resistance is read. The difference in resistance is essentially due to the part of the circuit made up of the electrolyte path (bone and tissue) between the silver electrode 18 and the tip of needle 58. Needle 58 is moved about on the skin surface until the lowest value of the resistance is measured. When this spot is located the conductivity meter is removed and the passive electrode 20 is embedded at that spot subcutaneously.

Figure 6:
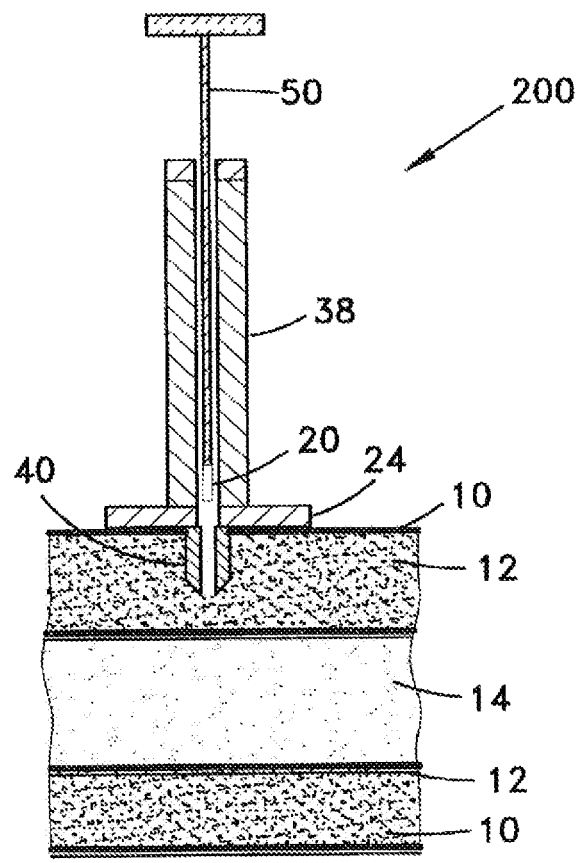
FIG. 6 schematically shows a device for embedding the passive electrode subcutaneously.

A device 200 for embedding the passive electrode subcutaneously is shown schematically in FIG. 6. Device 200 comprises a base 24 having a vertical hole bored through it. A trocar 40 and a hollow post 38 are rigidly attached coaxially with the hole to the lower and upper surface respectively as shown in the figure. In some embodiments base 24 has straps (not shown in FIG. 6) attached to it or another type of arrangement to stabilize device 200 on the surface of the skin and to prevent it from moving during the process of installing the electrode. Passing through post 38 is pusher 50. At the distal end of pusher 50 is the passive electrode 20, which is to be installed subcutaneously at the location determined as described herein above. Not shown in the figure is the insulated conducting wire that is connected to electrode 20 and passes through a channel in pusher 50. Pusher 50 may optionally be locked into an upper configuration in which the electrode 20 does not pass through the bottom of base 24 as shown in FIG. 6. When the base is pushed against the surface of the skin trocar 40 penetrates the tissue. The pusher is then unlocked and pushed downward injecting electrode 20 with the attached insulated conducting wire into the soft tissue, 12. The passive electrode is injected perpendicular to the skin then the device is tilted by 60-90 degrees such that it will be embedded subcutaneously roughly parallel to the skin surface. After the passive electrode 20 connected to the insulated electrode wire is delivered the trocar 40 is retracted from the tissue and device 100 is discarded. As described herein above with reference to apparatus 100, device 200 can also have fully manual embodiment; a semi-automatic embodiment, in which, for example, a mechanism based on a compressed spring can manually activated to release the spring and drive the pusher downwards; or may optionally be supplied with an electric motor and controller in a fully automatic embodiment. Device 200 is also designed for a single use only after which it should be discarded for the same reason as that described for apparatus 100.

Once both electrodes have been implanted, a power source is connected to the wires connected to electrodes 18 and 20. When the power source is activated, a current begins to flow through the tissue between the two electrodes.

The starting current is relatively low, on the order of less than 0.5 mA and is applied for a short period of time, on the order of 5 to 600 seconds. These parameters of the starting current should be appropriate to initiate the flow of the current in most situations. It is understood of course that the important parameter is the number of ions released during the start-up period and that this is proportional to the starting current multiplied by the time. Therefore the starting current may optionally be applied for longer or shorter periods of time than those suggested above if the value of the applied electrical current is varied accordingly.

According to the method described below, after the original brief starting period, the power source is removed and the conducting wires are disconnected from electrodes 18 and 20. Galvanic currents on the order of nanoamperes up to microamperes will continue to flow between active electrode 18 and the passive electrode 20 for a long period of time. The exact period of time depends on many factors, but the inventor believes that the right conditions can easily be created for the galvanic currents to continue for up to several years. The galvanic current causes a slow but continuous decomposition of the active electrode. As this electrode erodes, ions as well as nano-particles of the metal of which the active electrode is made are released into the surrounding tissue. If the active electrode is silver, then the silver ions kill the bacteria in the immediate vicinity of the electrode and gradually drift to other parts inside and eventually outside of the bone and from there to other parts of the body. At the same time the silver nano-particles also move slowly outward from the electrode and are gradually broken down in the body being slowly converted into silver ions.

In embodiments of the present invention, more than one passive electrode can optionally be implanted under the surface of the skin around the active electrode in the manner described herein above. The additional passive electrodes may be connected to the active electrode simultaneously, substantially simultaneously, or sequentially. This results in the establishment of galvanic currents between the "central" active electrode and the plurality of passive electrodes located around it, thereby increasing the volume of hard and soft tissue into which the ions from the active electrode are released.

Figure 7:
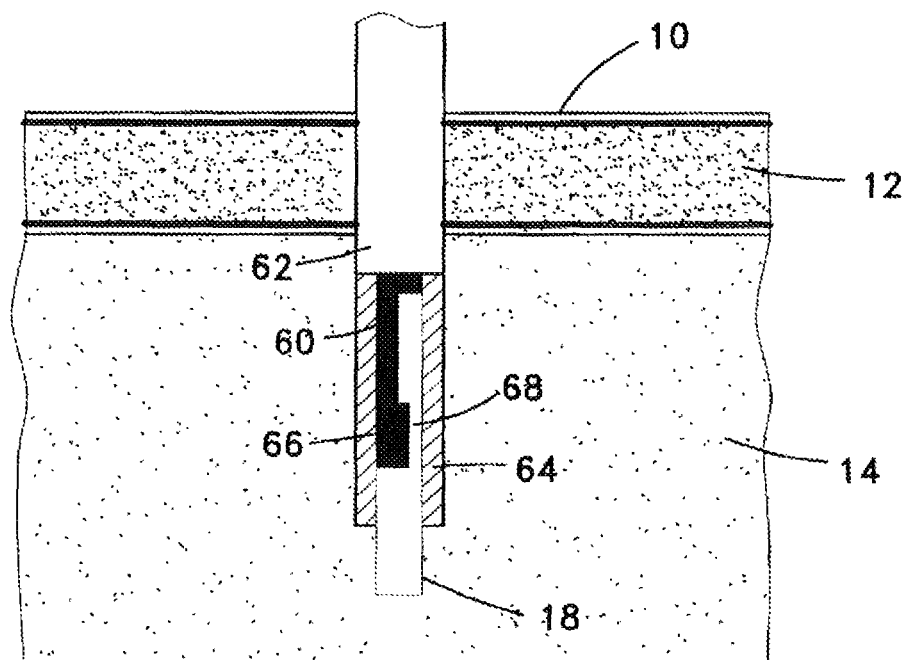
FIG. 7 schematically shows the connection between the active electrode and the conducting wire.

FIG. 7 schematically shows one embodiment of the connection between the active electrode 18 and the conducting wire 60. Approximately half of the top part of electrode 18 is removed to form a contact surface and a groove 68 is cut into it as shown in FIG. 7. The end of the conducting wire 60 is shaped in a similar fashion except that instead of a groove the contact surface at the end of the wire has a tongue 66 that projects outward from it. The insulation 62 is not bound to the conducting wire 60 but is rather a tight fitting sheath that may optionally be slid back and forth over the wire. Sliding the insulation over the end of the wire and upper part of the electrode presses the matching contact surfaces of the wire and electrode together to provide good mechanical and electrical contact between the two. The sheath additionally insures that tongue 66 remains fitted into groove 68, thereby preventing the electrode and wire from being pulled apart by an axial force and from being separated by sidewards forces. In order to make use of this method of connecting electrode 18 to the conducting wire 60, the bore 64 that was created in the bone 14, must have a diameter essentially the same as that of the electrode 18 in its lower part and a diameter essentially the same as the outer diameter of the insulation 62 in its upper part, as shown in FIG. 7. A bore that satisfies these conditions may optionally be created using a single shaft 42 (see FIG. 4) comprising sections having different diameters, wherein the diameter and length of each section is chosen to satisfy the dimensions of the electrode, insulation, and depth to which the electrode is to be implanted in the hard tissue for a given application.

Separating the wire from the electrode after the flow of the galvanic current between the active and passive electrodes is established is easily accomplished by pulling insulation 62 laterally and "wiggling" the wire until the tongue slips out of the groove allowing the wire to be withdrawn. If necessary the wire may optionally be reconnected to the electrode by reversing the process and using an appropriate visualization technique, e.g. x-rays, to find the exact location of the electrode.

The arrangement that is shown in FIG. 7 is also very important during the step of determining the correct location for implanting the passive electrode. The insulation 62 is pushed distally until all of the conducting wire 60 and the top part of electrode 18 are surrounded by an electrical insulation layer, thereby preventing at least some of the current from leaking and creating alternative paths between the passive electrode 18 and needle 58 (FIG. 5).

Since the hole that is created in the hard tissue has a diameter essentially equal to or only very slightly larger than the diameter of active electrode, the spongy bone tissue inside the hard outer shell of the bone will push against the sides of the electrode, holding it in place even before the tissue begins to re-grow around it. The effect is even greater, if a punch is used instead of a hole; since, in the former case, the punch tends to push through the spongy tissue to form the hole without removing all of the material as in the later case. Similarly the diameter of the upper part of the hole is essentially equal to the outer diameter of the insulation so that when apparatus 100 inserts the active electrode and attached insulated wire into the hole created in the hard tissue, the electrode becomes implanted in the body and will remain very stable from the moment of insertion and also the insulated wire will remain in electrical contact with the electrode during the stage of current initiation and subsequent measurements. The tight fit of both the active electrode and the insulation, make possible an embodiment of the connection between electrode and conducting wire that is similar to that shown in FIG. 7, with the exception that the tongue and groove connection is not needed. The matching surfaces on the respective ends of the electrode and wire may optionally be planar and the two are held in electrical contact by the force of the walls of the insulating sheath pushing them against each other. The tight fit of the end of the insulation prevents it from accidentally being pulled out of the hole; however the insulation may optionally be removed from the hole and the wire disconnected from the electrode when desired by intentionally pulling the insulation and wire proximally.

The same arrangement employing an insulating sheath as described herein above with respect to the active electrode is also used to connect the passive electrode delivered, which is embedded under the skin, to an electrical conducting wire.

Figure 9A:
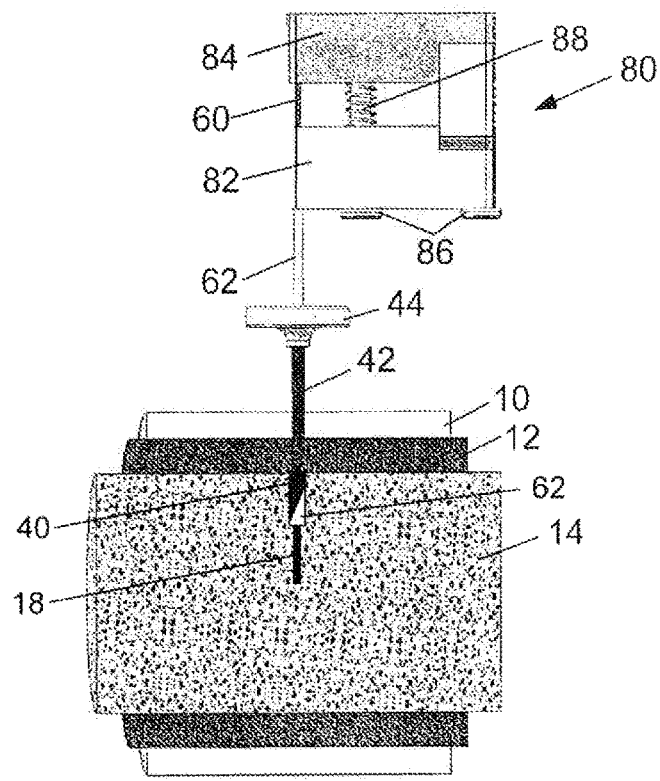
FIG. 9A and FIG. 9B schematically show a clamp that has been devised to assist the operator to disconnect the conducting wire from an implanted electrode.
Figure 9B:
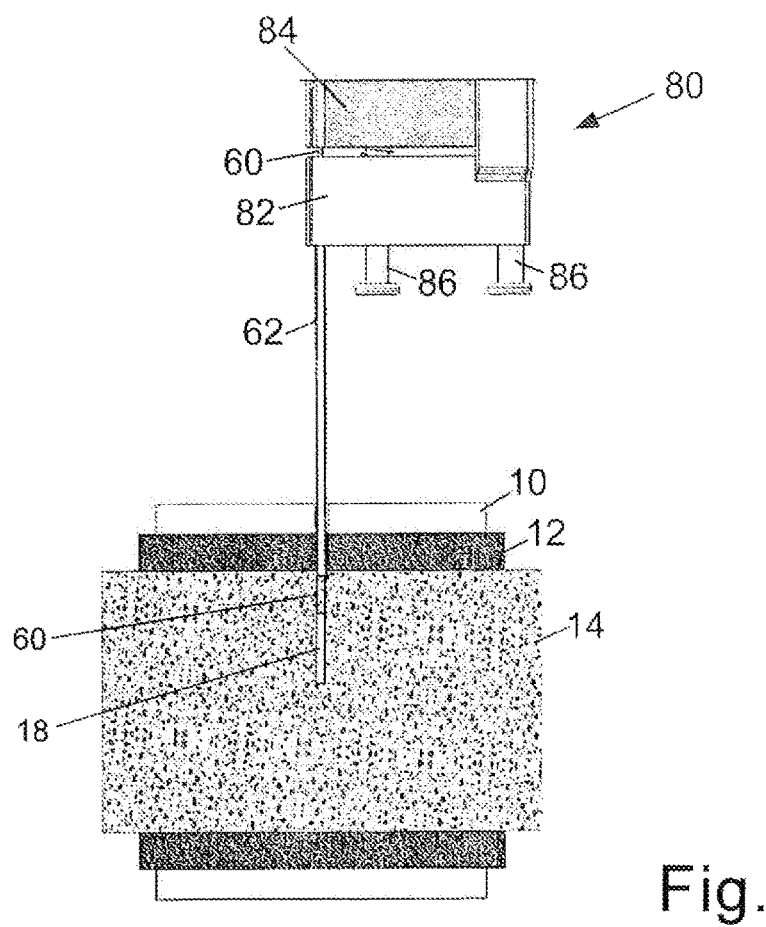

As said, the tight fit of the end of the insulation prevents it from accidentally being pulled out of the hole in the hard tissue, thereby disconnecting the conducting wire from the electrode. FIG. 9A and FIG. 9B schematically show a clamp 80 that has been devised to assist the operator to disconnect the conducting wire 60 from an implanted electrode 18. Clamp 80 comprises a lower part 82 to which the proximal end of the insulating sheath 62 is firmly clamped and an upper part 84 to which the proximal end of the bare conducting wire is firmly clamped. The two parts of the clamp are connected together by posts 86 on which the lower part 82 can slide relative to the upper part 84. A spring 88 is fit over each post 86 between the two parts of clamp 80 holding them apart when inserting the electrode in the body as shown in FIG. 9A. To disconnect and remove wire 60 and leave electrode 18 embedded in the hard or soft tissue the lower part 82 of clamp 80 is pulled towards the upper part compressing springs 88 as shown in FIG. 9B. When this is done the insulation sheath 62 will be pulled proximally relative to conducting wire 60, thereby uncovering the connection between the electrode 18 and the wire 60. The wire together with the insulation sheath can now be removed from the body leaving the electrode stably implanted in hard or soft tissue.

Figure 8:
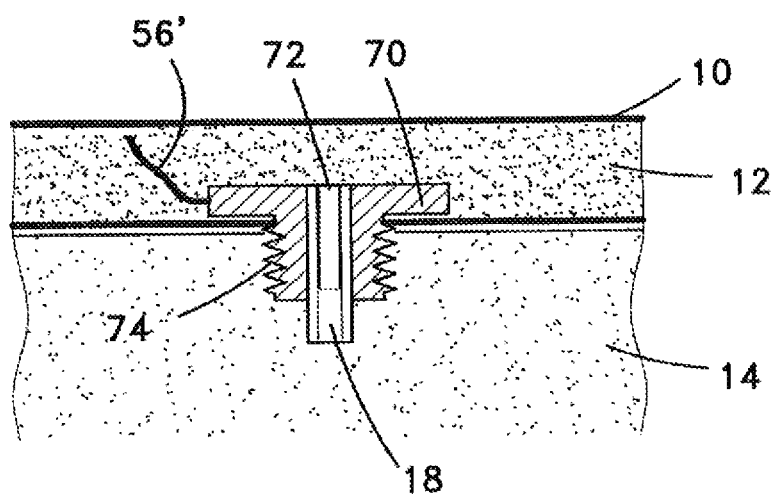
FIG. 8 shows schematically an embodiment of the control unit that may optionally be fixed to a bone.

An embodiment of the control unit 70 that may optionally be fixed to a bone 14 is shown schematically in FIG. 8. As previously described, control unit 70 controls the amount of active ions being released by controlling the current flow. In this embodiment the control unit 70 is implanted during a standard surgical procedure that is usually done in cases of bone infections, e.g. surgical debridement. In such procedures the bone is exposed and the control unit and active electrode may optionally be implanted during the same surgery with or without the use of apparatus 100. The housing of the control unit is either made of or externally covered by an electrically insulating biocompatible material. On the bottom center of the housing of control unit 70 is a projection 74 that has threads on its outer surface. A hole having a diameter slightly larger than that of the active electrode is bored through the center of the control unit 70 and projection 74. Using a standard orthopedic technique the threaded projection 74 is screwed into the bone above the location where the active electrode is to be implanted. A hole is then drilled or punched into the bone through hole 72 and active electrode 18 is inserted into the bone. The upper part of electrode 18 is in electrical contact with the inner wall of hole 72 of control unit 70 to connect electrode 18 with the electrical circuitry in the control unit. The electrical contact may optionally be improved by many techniques known in the art, e.g. one or more spring loaded pins may optionally be positioned inside hole 72. After it is implanted in the bone, the active electrode 18 is connected to the passive electrode (not shown in FIG. 8) via the circuitry in the control unit and insulated wire 56'. In this embodiment both active and passive electrodes are permanently connected to the electronic circuitry inside the control unit. In an embodiment of the controller that is attached to the bone, the passive electrode is fixed to the control unit or alternatively the external upper surface of the control unit is coated in part by the material of the passive electrode, so that the coating itself forms the passive electrode. The coating is electrically connected to the control unit.

In an embodiment of the control unit that is to be implanted subcutaneously the passive electrode may optionally be attached to or created on the surface of the housing of the control unit eliminating the need for a separate passive electrode. Creating the passive electrode on the surface of the housing is accomplished by coating a part of the outer surface of the housing with a layer of the metallic material of the passive electrode and the remainder of the surface is coated with an electrically insulating material. The coating of metallic material is electrically connected to the circuitry inside the control unit. The control unit will be implanted subcutaneously by slicing open the skin in the normal manner. The active electrode is implanted in the hard tissue using apparatus 100 and electrically connected to the control unit by an insulated conducting wire as described herein above.

Active electrodes made of metallic silver can serve the additional mechanical function of acting as a fiducial marker. Fiducial markers are attached to or implanted into the patient in scanned regions of the body to provide a reference frame for comparing images formed at different times and for comparing images formed from different imaging modalities, e.g. CT and X-Ray images. Fiducial implanted markers have been used in orthopedic surgery (knee, hip and spine) to allow alignment of pre-operative CT scans and/or X-ray radiographs, in order to increase the accuracy of such procedures. Metallic radiopaque pins, e.g. titanium screws, are used as fiducial markers and are implanted by pre-operative short surgical procedures typically lasting 15-30 min. These additional operations are often associated with patient discomfort, increased operating times and higher overall cost. Markers are used in other applications as well, as for example, in breast biopsies. Metallic markers are implanted at the appropriate site for future identification of the biopsied area. Foreign body granulomas formed around the implants and low accuracy are among the problems associated with metallic implanted biopsy markers.

An active silver electrode implanted by the methods and apparatus described herein can also function as a fiducial marker which may optionally be implanted or injected within or near the target site with minimal disruption or destruction of patient tissue, which will remain stably fixed at precise body positions from the time that preoperative images are taken to the time of the intraoperative procedures or follow-up imaging and which is biocompatible and partial or completely degradable, thus eliminating the need for subsequent removal out of the body.

In this application, the silver implant functions as a radiopaque marker also having an antibacterial characteristic, guarding it from infections. In the prior art, when fiducial implants are implanted in an infected area such as a bone, a bacterial biofilm often is created on the implant surface, which eventually causes further infection of the region. Therefore it is possible but it is not indicated to use fiducial implants in infected bones since frequently an infection develops in patients that were given an implant in an orthopedic surgery and the implant must be removed in a later procedure and the infection treated. These complications may optionally be avoided by using the apparatus and techniques described herein above to implant an active silver electrode as a fiducial marker with a passive electrode functioning as an accessory, which facilitates a very slow release of silver ions from the silver marker to maintain a long term bactericidal effect around the marker.

Figure 10A:
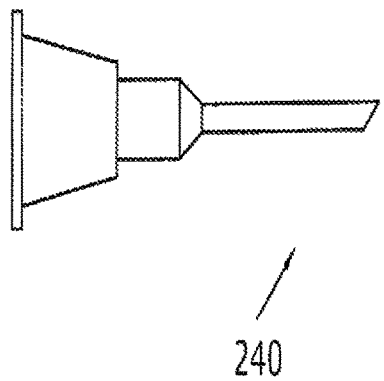
Figure 10B:
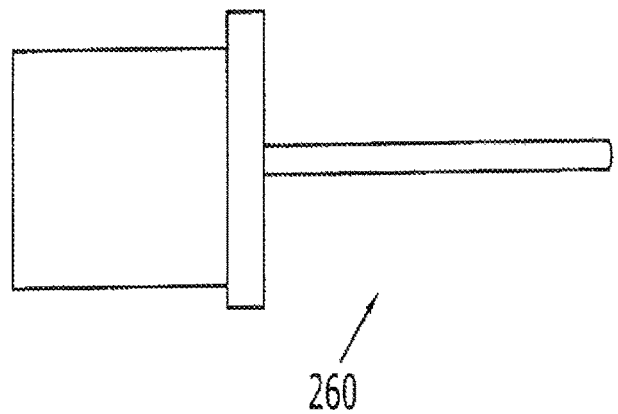
Figure 10C:
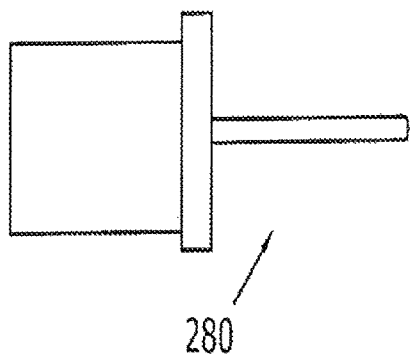
Figure 10D:
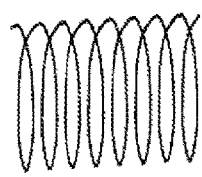

FIGS. 10A to 10H schematically show the components of the apparatus of the invention according to at least some embodiments. In these figures: FIG. 10A shows a trocar 240; FIG. 10B shows a punch (or drill) 260; FIG. 10C shows a pusher 280; FIG. 10D shows silver electrode 18; FIG. 10E shows temporary electrode 300; FIG. 10F is an external D.C. voltage source 22; FIG. 10G shows conductivity meter 38, with needle 400 connected to it; and 10H is the second electrode 20. Design features and the function of each of these components will be described herein below with reference to FIGS. 10 to 19, which schematically illustrate the steps of the method of the invention.

To insure sterility, all components of the apparatus are supplied in a "factory-sealed" container, which is opened by the surgeon at the time of performing the procedure. Of course it is also possible that each of the components will be individually wrapped in a sealed "envelope" to maintain its sterility until it is used. It is anticipated that the apparatus will be supplied in two embodiments—a "starter" apparatus, which contains all of the components shown in FIGS. 10A to 10H; and a "basic" apparatus which contains all components of the "starter" apparatus with the exception of external D.C. voltage source 22 and conductivity meter 380, which are relatively expensive and clearly reusable. Electrodes 18 and 20 remain inside the body of the patient, but all other components of the basic apparatus are preferably disposed of after a single use.

FIG. 11 shows the first step of the procedure. After using conventional means to locate the infected area 16 inside bone 14 (or joint), trocar 240 is pushed through the skin 10 and layer of muscle 12 contacting the edge of the bone 14 near the center of the infected area. Trocar 240 is a standard trocar used for orthopedic procedures, but it, like other components of the apparatus, can possibly be made to less demanding standards concerning material and strength since it is not meant to be re-sterilized or reused.

Figure 12:
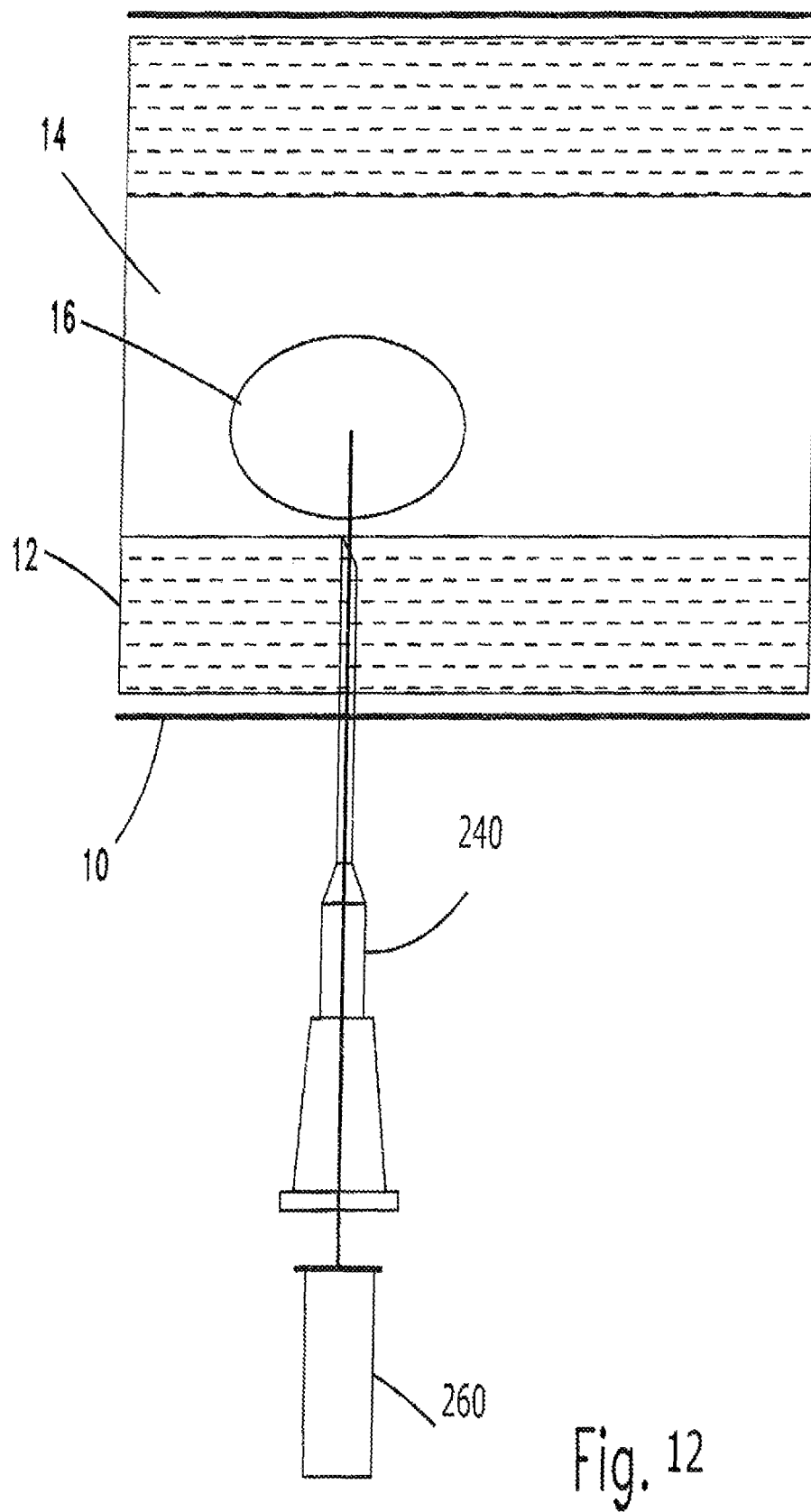
Figure 13:
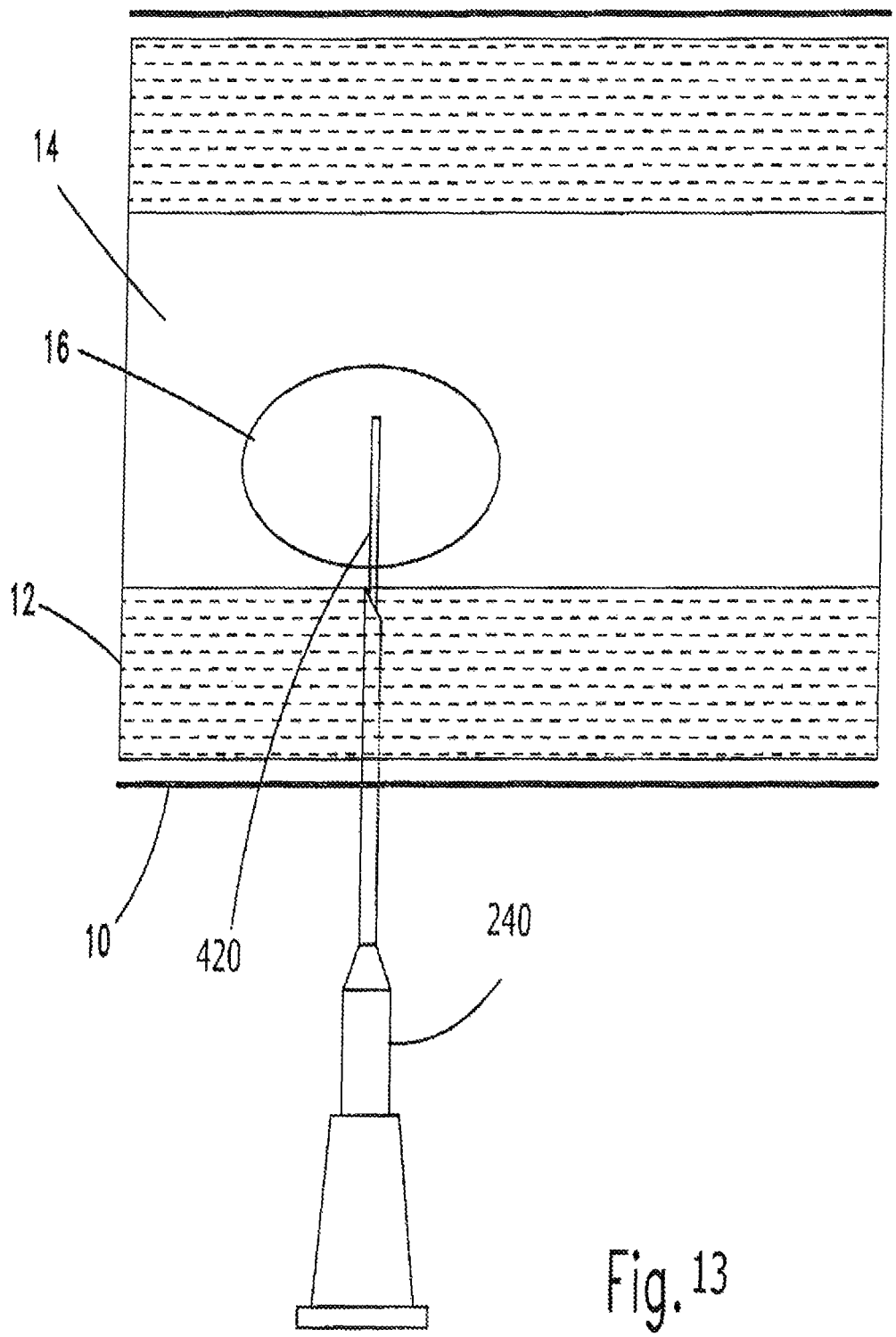

In the step shown in FIG. 12 a hole is made in bone 14 by means of an orthopedic bone punch 260 inserted through trocar 240 and pushed through bone 12 into the infected area 16. In some situations it might be preferable to use a small diameter bone drill instead of a punch. In either case, FIG. 13 shows the situation after the punch/drill 260 has been withdrawn. There remains, at the end of trocar 240, a hole 420 that penetrates the bone and extends into infected area 16.

Figure 14:
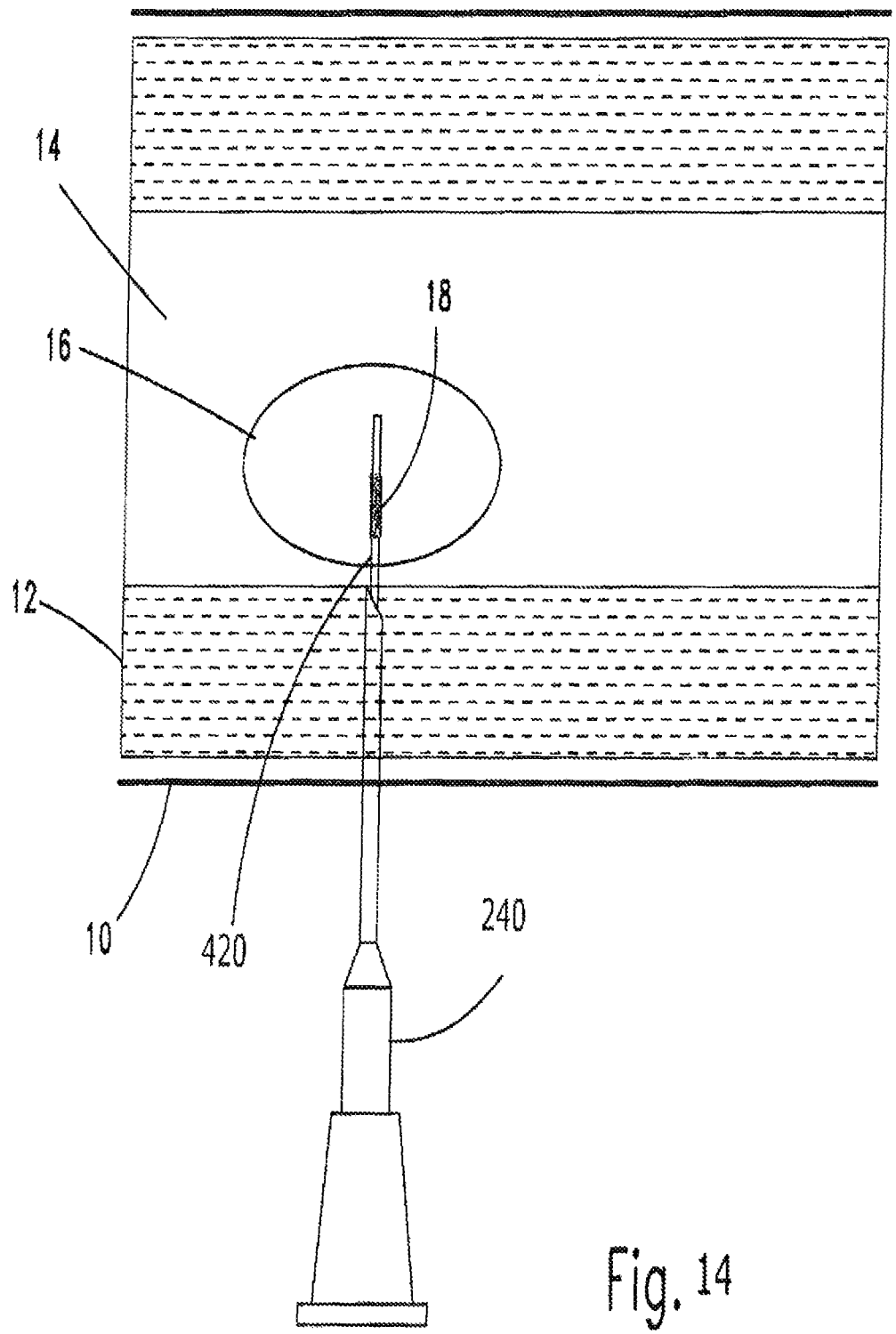

In the next step, the result of which is shown in FIG. 14, pusher 280 (FIG. 10C—not shown in FIG. 14) is used to push silver electrode 18 through trocar 240 to the end of hole 420 that was previously made in bone 14. The pusher is a simple rod or pipe with a plastic handle that can slide through the trocar.

The silver electrode 18 is a small piece of pure silver or a silver containing alloy that typically weighs on the order of 1-50 mg. Silver electrode 18 can be supplied as a small solid piece of metal or preferably is fabricated from silver wire into a small diameter cylindrical coil as shown in FIG. 10D. The hole 420 has a diameter only very slightly larger than the diameter of silver electrode 18 so that the spongy bone tissue inside the hard outer shell of bone 14 will push against silver electrode 18, holding it in place even before the tissue begins to re-grow around it. The effect is even greater, if a punch is used instead of a hole; since, in the former case, the punch tends to push through the spongy tissue to form the hole without removing all of the material as in the later case.

This is an appropriate place to note that none of the figures are drawn to even an approximate scale and that the scale varies from figure to figure. The actual sizes of the various components of the apparatus can be determined by starting with the diameter of silver electrode 18, which is slightly less than the diameter of hole 420, which is equal to the outer diameter of punch 260, etc. It also should be noted that, although the preferred location of the silver electrode for the treatment of osteomyelitis is within the infected area in the bone, in other circumstances other locations in the body in the vicinity of the infected area, e.g. in the metaphysis of a bone might be the preferred location.

Figure 15:
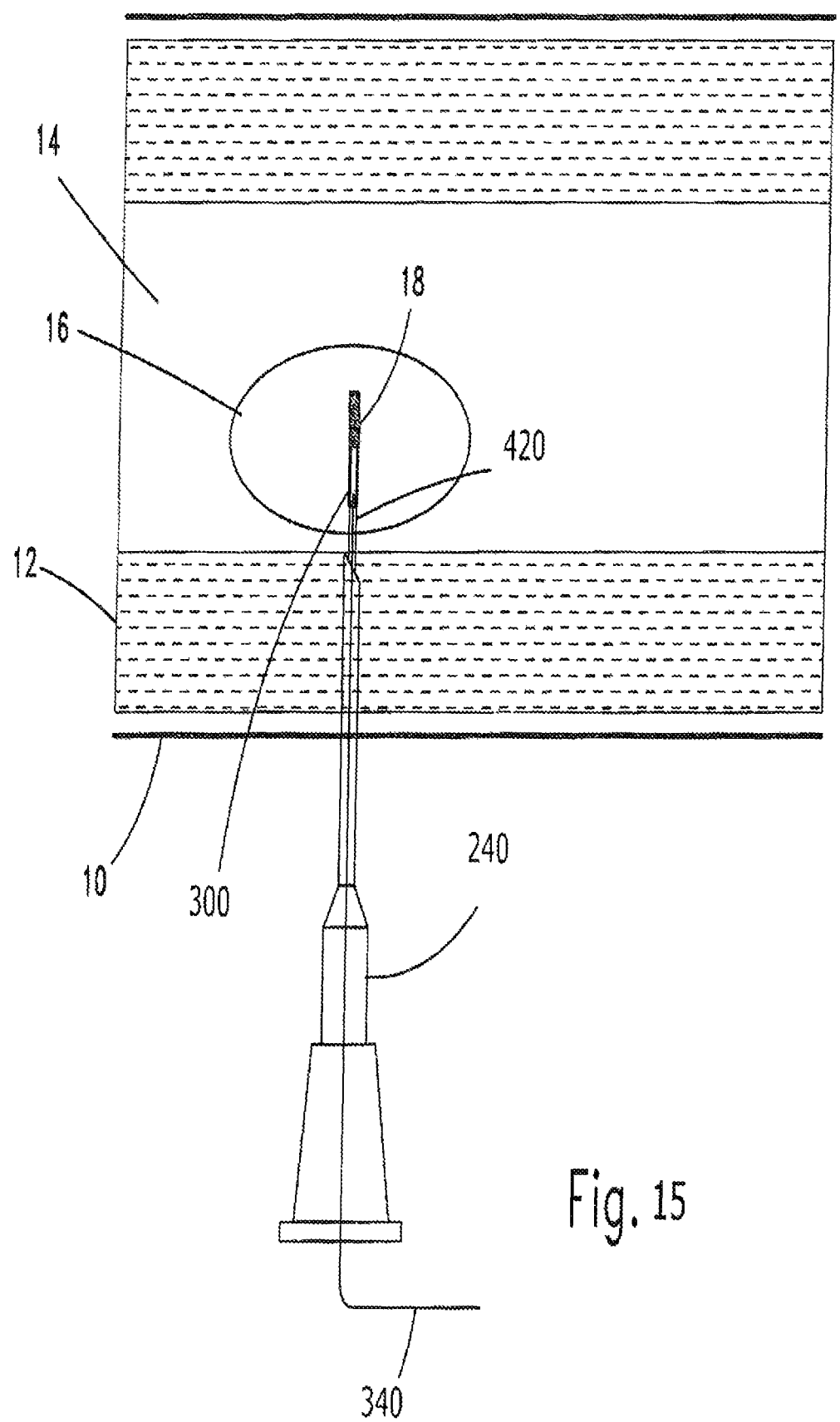

After silver electrode 18 is positioned in hole 420, temporary electrode 300 is inserted into hole 420 on top of silver electrode 18 with the aid of pusher 280. As can be seen in FIG. 10E, temporary electrode 300 is comprised of a small metallic cylinder 320 connected to a long insulated electricity conducting wire 340. Metal cylinder 320 is surrounded on all but its bottom surface by an electrically insulating layer 360, whose purpose will be explained herein below. As can be seen in FIG. 15, after pusher 280 has been withdrawn, the exposed bottom surface of metallic cylinder 320 of temporary electrode 300 is in contact with the top of silver electrode 18 and the free end of electricity conducting wire 340 extends outside of trocar 240.

Figure 16:
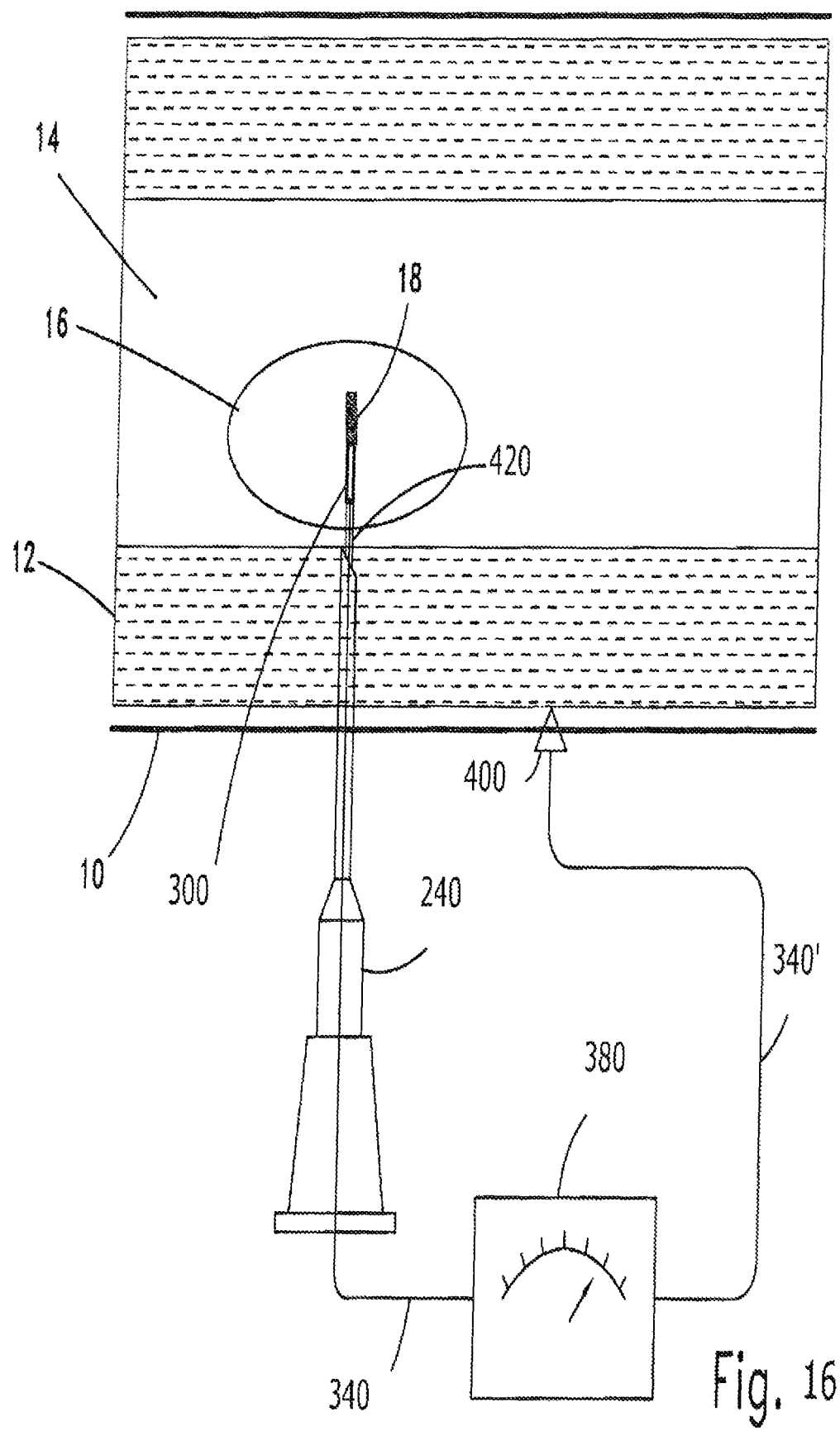
Figure 17:
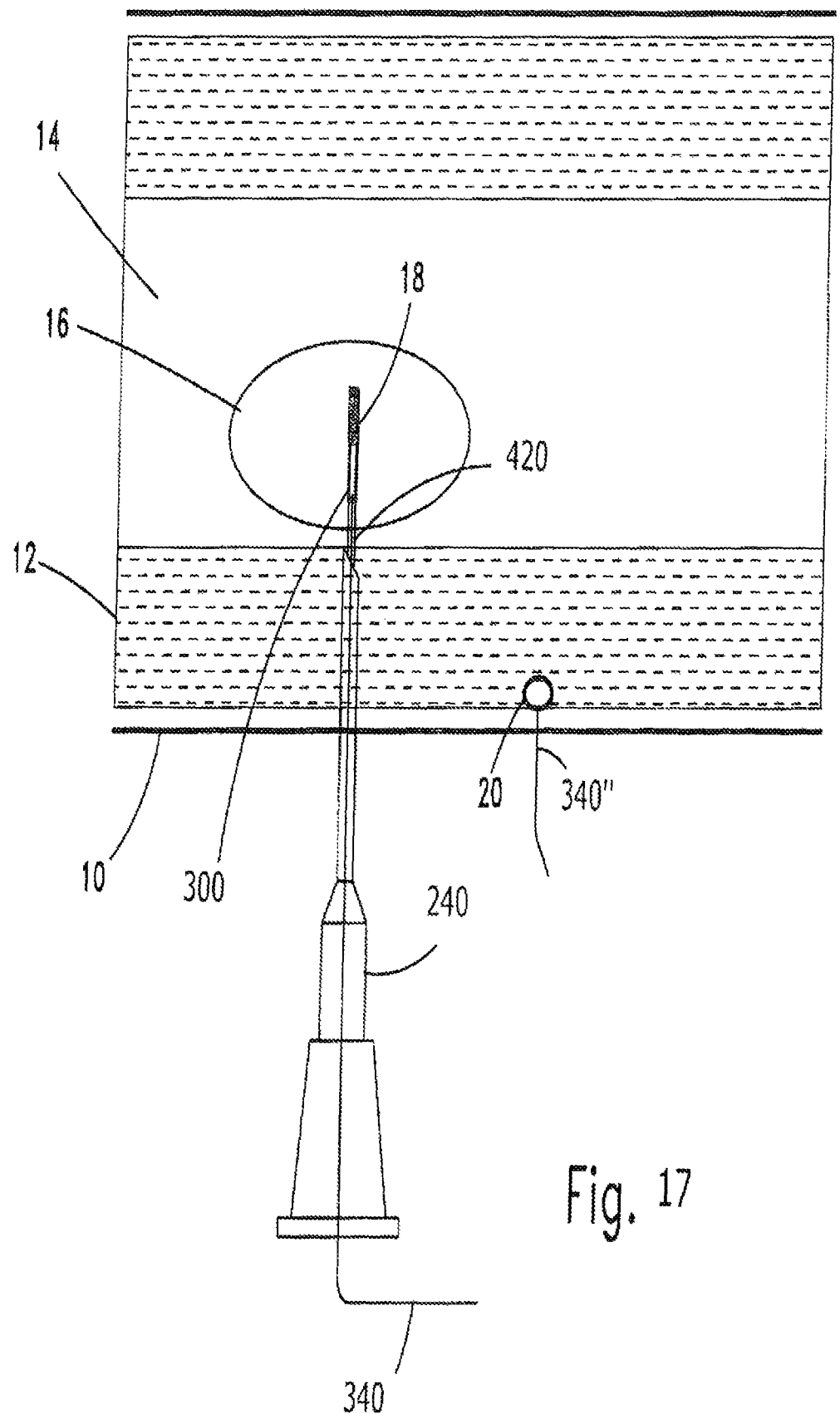
Figure 18:
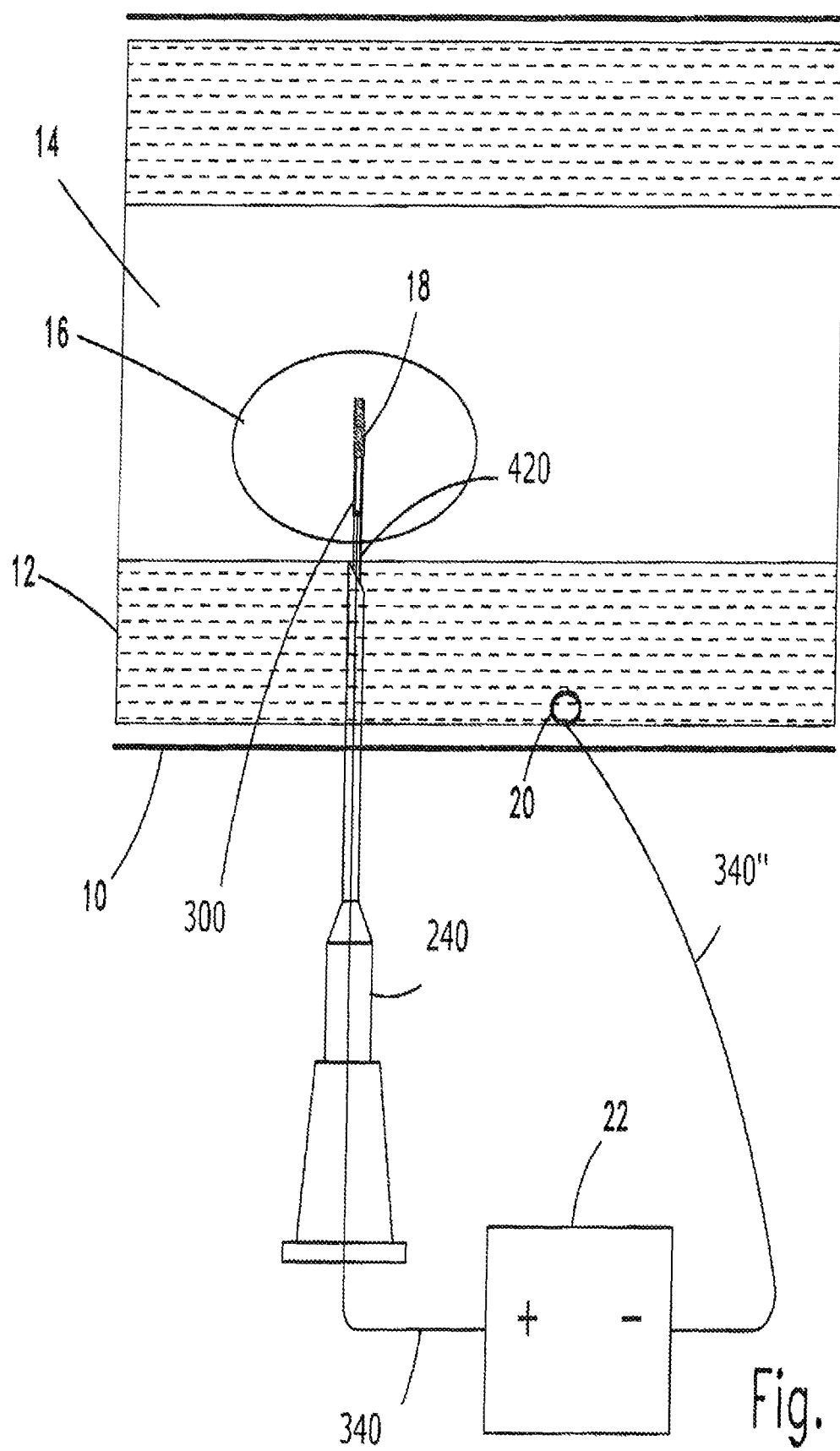
Figure 19:
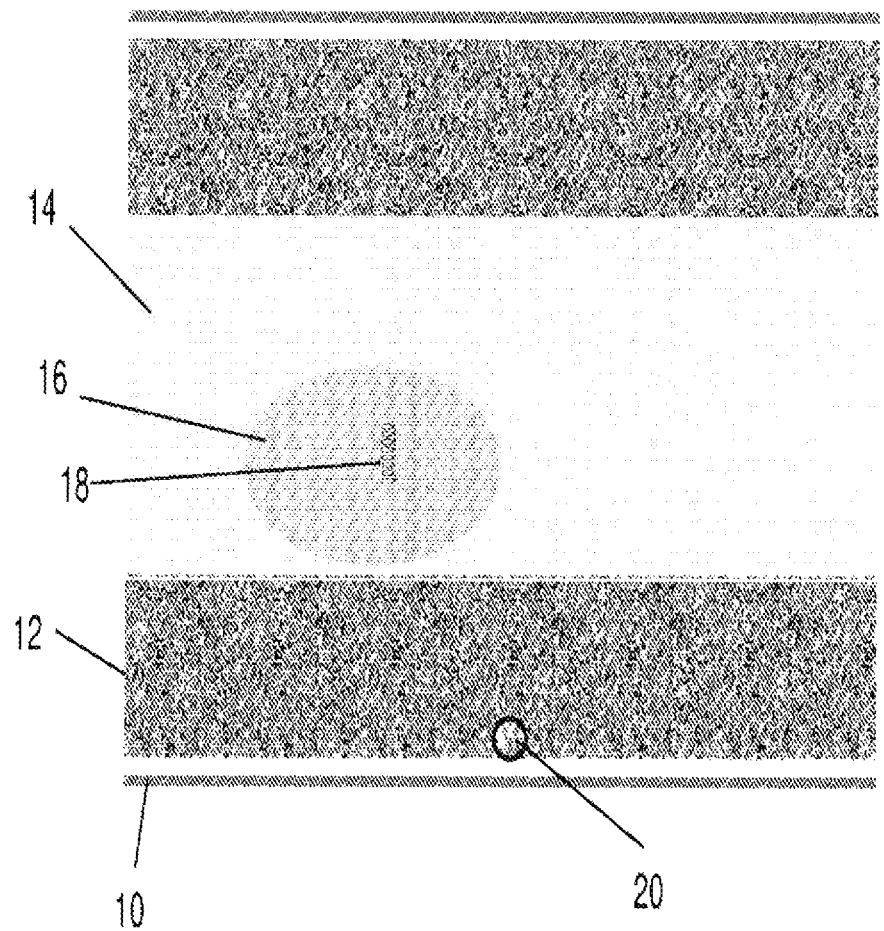

The next step is to determine the location of the second electrode. According to the invention, the most effective results will be obtained if the second electrode is placed at the location under the surface of the skin at which the electrical conductivity between the second electrode and the silver electrode is maximized. FIG. 16 illustrates the method for locating the optimal position for placement of the second electrode. One terminal of conductivity meter 380 is connected to electrically conducting wire 340 of temporary electrode 300, which is in electrical contact with silver electrode 18, embedded in infected area 16 of bone 14. The other terminal of conductivity meter 380 is connected to electrically conducting wire 340', which has a needle 400 attached to its end. Needle 400 is made of the same material as is the second electrode. When needle 400 touches the skin a closed circuit is set up and the meter reads the conductivity of the circuit. If the needle is moved to a different location a different conductivity is read. The difference in conductivity is essentially due to the part of the circuit made up of the electrolyte path (bone and tissue) between the silver electrode 18 and second needle 400. Needle 400 is moved about on the skin surface until the highest value of the conductivity is measured. When this spot is located the conductivity meter is removed and the second electrode 20 is embedded subcutaneously. This is the stage of the procedure that is shown in FIG. 17.

Second electrode 20 is a small, typically 5-100 mg piece of biocompatible material that must have a negative electrical potential with respect to silver. An example of such a material is gold.

Once both electrodes have been implanted, D.C. voltage source 22 is connected to wire 340 of temporary electrode 300 and to electrically conducting wire 340" connected to second electrode 20 as shown in FIG. 12. When voltage source 22 is activated, a direct current from voltage source 22 begins to flow through the tissue between the two electrodes as shown above and described hereinabove. It is now apparent why the insulation layer 360 is necessary on temporary electrode 300. If it were not present, then at least some of the current would leak from the sides of the temporary electrode, creating alternative paths to the second electrode.

The starting current is relatively low, on the order of less than 0.5 mA and is applied for a short period of time, on the order of 5 to 120 seconds. These parameters of the starting current should be appropriate to start the flow of the current in most situations. It is understood of course that the important parameter is the number of ions released during the start-up period and that this is proportional to the starting current multiplied by the time. Therefore the starting current can be applied for longer or shorter periods of time than those suggested above if the value of the applied electrical current is varied accordingly.

After the original brief starting period, the D.C. voltage source 22, temporary electrode 300, and trocar 240 are removed. Wire 340" is removed from second electrode 20.

Galvanic currents on the order of a couple of tens of nanoamperes will continue to flow between silver electrode 18 and second electrode 20 for a long period of time. The exact period of time depends on many factors, but the inventor believes that the right conditions can easily be created for the galvanic currents to continue for an extended period of time, even up to a number of years. The galvanic current causes a slow but continuous decomposition of the silver electrode. As this electrode erodes, silver ions as well as nano-particles of silver metal are released into the surrounding tissue. The silver ions kill the bacteria in the immediate vicinity of the electrode and gradually drift to other parts inside and eventually outside of the bone and from there to other parts of the body, where they act as a bactericide for any bacteria that they encounter. At the same time the silver nano-particles also move slowly outward from the electrode and are gradually broken down in the body being slowly converted into silver ions.

In another embodiment of the invention the silver electrode is not made of pure silver, but of an alloy of silver with a small percentage of the material used to make the second electrode. In this embodiment, the erosion of the electrode by the galvanic current will result in the release of silver ions and nano-particles of the alloy. As the nano-particles of alloy move around in the body, conditions will arise wherein pairs of them will form nano-size galvanic cells, which will release even more silver ions both locally and eventually in all parts of the body.

In another embodiment of the invention, additional second electrodes can be implanted under the surface of the skin around the silver electrode in the manner describer herein above. This results in the establishment of galvanic currents between the "central" silver electrode and the plurality of second electrodes located around it, thereby increasing the volume of bone and tissue into which the silver ions are released.

The invention has been illustrated in terms of treatment of an existing case of Osteomyelitis, but it could also have an important role in preventing bacterial disease. For example, it is known that Osteomyelitis develops after a significant percentage of orthopedic procedures, sometimes after an extended period when it is felt that the procedure has been a complete success. The cost and complexity of the method of the present invention is so small relative to that of most orthopedic procedures and certainly when compared to the long term cost and difficulty of treating a patient who is unfortunate enough to contract Osteomyelitis, that serious consideration should be given to making the use of the invention part of the protocol of many orthopedic procedures by not waiting for infection to set in but by implanting a silver electrode in the bone being treated and carrying out the rest of the steps of the invention as part of the post surgery closing up of the wounds.

The safety and feasibility of the silver ions bone infection treatment of the invention have been demonstrated in-vivo by inducing OM in animals by bacteria inoculation and applying the method of the invention to cure them. Rabbits were used for this study as they are a frequently used animal model in OM research.

The study had three stages. In the first stage safety was demonstrated, by applying the method of the invention to healthy animals in comparison to a control group of healthy and untreated animals. The safety of the method was proven in 100% of the animals by X-Ray, blood tests, gross pathology and histology.

In the second stage the model of inducing well developed bone infection in animals was established, by employing different inoculations.

Finally, in the third stage the feasibility of the method was demonstrated. The right tibia of each of the animals from both the treatment and the control group was inoculated with *Staphylococcus aureus*. After one week the method of the invention was applied to the animals of the treatment group. Half of the animals from both groups were sacrificed at the end of follow-up periods, of 2 and 4 weeks The X-ray and histology analysis showed that at the end of the follow-up period all of the untreated animals had acute OM, characterized by abscesses formation within the medullary cavity. These findings are indicative that the establishment of the model was successful and self healing did not occur.

In the majority of the treated animals in the long term follow-up group, an apparent reduction in the size of the intramedullary abscess was noted. In one animal complete healing was observed. In the animals of the short term follow-up, the start of a healing process has been observed in about half of the animals.

At this stage additional safety evidence was provided by blood tests, gross pathology and histological analysis performed in all animals, to demonstrate that the quantities and nature of the elements used (silver and complementary) did not affect the general health of the animals.

Although embodiments of the invention have been described by way of illustration, it will be understood that the invention may be carried out with many variations, modifications, and adaptations, without exceeding the scope of the claims.

The invention claimed is:

1. An apparatus for activating and operating an implantable battery inside a human or animal body, said apparatus comprising:
   (a) at least two electrodes adapted to be implanted in said body, of which at least a first electrode being an active electrode composed of a metallic material and a second electrode being a passive electrode composed of a material whose electrical potential is negative relative to an electrical potential of said active electrode;
   (b) an external power source;
   (c) a slidable tight-fitting sheath;
   (d) at least one electrically conducting wire; and
   (e) a control unit configured to automatically control an output of said power source, to:
      (i) apply an initiation current to said active electrode in the order of less than 0.5 mA, to boost a release of metallic ions from said active electrode, and
      (ii) discontinue the initiation current after 5 to 600 seconds,
   wherein the boosted release of metallic ions allows metallic ions to slowly release from said active electrode absent any application of current from said power source, and
   wherein said active electrode being in electrical communication with said passive electrode via said electrical conducting wire, said electrical conducting wire having:
      a first contact surface at one end being in physical and electrical contact with said passive electrode, and
      a second contact surface at a second end of said electrical conducting wire being in physical and electrical contact with a contact surface of said active electrode,
      said second contact surface of said electrical conducting wire and said contact surface of said active electrode each having a groove and tongue geometry, said surfaces being mutually complementary such that when pressed together by said tight-fitting sheath, said second contact surface and said contact surface of said active electrode are locked with no axial movement therebetween.

2. The apparatus of claim 1, wherein said tight-fitting sheath of insulating material is slidable from a covered state in which said second contact surface and said contact surface of said active electrode are pressed and locked, to an uncovered state in which physical and electrical contact between said contact surface of said active electrode and said second contact surface of said electrically conducting wire is broken.

3. The apparatus of claim 1, wherein the active electrode comprises one of the following: silver, iron, zinc, or magnesium.

4. The apparatus of claim 1, wherein the active electrode is made of silver or a silver alloy and the passive electrode is made of gold or platinum.

5. The apparatus of claim 1, wherein the active electrode is made of iron, zinc, or magnesium and the passive electrode is made of gold.

6. The apparatus of claim 1, wherein the control unit and the power source are external to the body.

7. The apparatus of claim 1, wherein the control unit and the power source are adapted for implantation in one or more of the following locations inside the body: subcutaneously, muscle, fat, hard tissue, bone, and cartilage.

8. The apparatus of claim 7, wherein the control unit is encased in a housing; and the passive electrode is incorporated onto a surface of the housing by coating a part of said surface with a layer of the metallic material of said passive electrode and the remainder of said surface is coated with an electrically insulating material.

9. The apparatus of claim 1, wherein the active electrode is a pin made of metallic silver and the passive electrode functions as an accessory, which facilitates a very slow release of silver ions from said pin to maintain a long term bactericidal effect around said pin.

10. The apparatus of claim 1, wherein the control unit comprises one or more of the following components:
- a resistance meter adapted to measure resistance between the active electrode and the passive electrode;
- a voltmeter adapted to measure a voltage difference between said active electrode and said passive electrode;
- a processor adapted to control a supply of applied current by
  a) comparing measured values of a metallic ion current from said active electrode to a pre-set threshold; and
  b) activating the power source to increase the release of ions if said measured metallic ion current is lower than said threshold;
- a memory component to store data recorded by said control unit;
- a transmitter/receiver component for communication with a remote processing and display subsystem; and
- a housing.

11. The apparatus of claim 10, wherein the power source is located within the housing of the control unit and said power source is adapted to supply a starting or maintenance current to release ions from the active electrode and to supply electrical power to other components of the control unit.

12. The apparatus of claim 10, wherein the control unit is adapted to be implanted in the body and has a rounded form and small dimensions, with a diameter less than 2.5 cm and thickness less than 3 mm.

13. The apparatus of claim 12, wherein a bottom center of the housing of the control unit comprises a projection having threads on its outer surface, thereby allowing said control unit to be attached to hard tissue.

14. The apparatus of claim 13, wherein the passive electrode is created on a surface of the housing by coating a part of said surface with a layer of a metallic material of said passive electrode and a remainder of said surface is coated with an electrically insulating material, thereby eliminating the need for a separate passive electrode.

15. The apparatus of claim 1, wherein the power source is adapted to supply DC power, or AC power, or both and is also adapted to supply said power at different frequencies and having different waveforms.

16. The apparatus of claim 15, wherein the waveforms are chosen from: sinusoidal, triangular, and square.

17. The apparatus of claim 15, wherein the power can supply electric current, an electrical potential difference, or both.

18. The apparatus of claim 15, wherein an AC power source comprises components that are adapted to scan a range of frequencies to find the frequency that provides the best ratio of voltage to metallic ion current.

* * * * *